(12) United States Patent
Dalal et al.

(10) Patent No.: US 11,642,248 B2
(45) Date of Patent: May 9, 2023

(54) ABSORBENT ARTICLE WITH AN EAR PORTION

(71) Applicant: The Procter & Gamble Company, Cincinnati, OH (US)

(72) Inventors: Urmish Popatlal Dalal, Milford, OH (US); Todd Douglas Lenser, Liberty Township, OH (US); Joerg Mueller, Karben (DE)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 101 days.

(21) Appl. No.: 15/674,559

(22) Filed: Aug. 11, 2017

(65) Prior Publication Data

US 2018/0042777 A1 Feb. 15, 2018

Related U.S. Application Data

(60) Provisional application No. 62/374,286, filed on Aug. 12, 2016.

(51) Int. Cl.
*A61F 13/15* (2006.01)
*A61F 13/58* (2006.01)
(Continued)

(52) U.S. Cl.
CPC .... *A61F 13/15203* (2013.01); *A61F 13/4902* (2013.01); *A61F 13/49058* (2013.01);
(Continued)

(58) Field of Classification Search
CPC .......... A61F 13/15203; A61F 13/49058; A61F 13/4902; A61F 2013/49047;
(Continued)

(56) References Cited

U.S. PATENT DOCUMENTS 3,113,225 A 12/1963 Kleesattel et al.
3,338,992 A 8/1967 Allison
(Continued)

FOREIGN PATENT DOCUMENTS

CN 103237533 A 8/2013
CN 104837455 B 4/2018
EP 1256594 A1 11/2002
EP 1447066 A1 8/2004
(Continued)

OTHER PUBLICATIONS

International Search Report, PCT/US2017/046397, dated Sep. 28, 2017, 13 pages.
(Continued)

*Primary Examiner* — Adam Marcetich
*Assistant Examiner* — Meagan Ngo
(74) *Attorney, Agent, or Firm* — Sarah M. DeCristofaro; Wednesday G. Shipp

(57) ABSTRACT

An absorbent article includes a first waist region, a second waist region, and a crotch region disposed between the first and second waist regions. The article further includes a chassis comprising a topsheet, a backsheet, and an absorbent core disposed between the topsheet and backsheet; and an ear. The ear includes a laminate having a first nonwoven and second nonwoven and an elastomeric material sandwiched between said first and second nonwovens. The laminate comprises a plurality of ultrasonic bonds. The ear also has a first inelastic region and an elastic region. The ear is joined to the chassis in the first inelastic region, and a fastening system is joined to the ear in the elastic region.

19 Claims, 9 Drawing Sheets

(51) Int. Cl.
*A61F 13/56* (2006.01)
*A61F 13/49* (2006.01)

(52) U.S. Cl.
CPC .......... *A61F 13/5633* (2013.01); *A61F 13/58* (2013.01); *A61F 2013/15406* (2013.01); *A61F 2013/15552* (2013.01); *A61F 2013/49047* (2013.01)

(58) Field of Classification Search
CPC .. A61F 2013/15552; A61F 2013/15406; A61F 13/5633; A61F 13/581; A61F 2013/588; A61F 13/62; A61F 13/5644; A61F 2013/586; A61F 2013/587; A61F 13/58–581; A61F 2013/285–588
See application file for complete search history.

(56) References Cited

U.S. PATENT DOCUMENTS

| | | |
|---|---|---|
| 3,562,041 A | 2/1971 | Robertson |
| 3,566,726 A | 3/1971 | Politis |
| 3,692,613 A | 9/1972 | Pederson |
| 3,733,238 A | 5/1973 | Long et al. |
| 3,802,817 A | 4/1974 | Matsuki |
| 3,848,594 A | 11/1974 | Buell |
| 3,849,241 A | 11/1974 | Butin |
| 3,860,003 A | 1/1975 | Buell |
| 3,911,173 A | 10/1975 | Sprague, Jr. |
| 3,929,135 A | 12/1975 | Thompson |
| 4,116,892 A | 9/1978 | Schwarz |
| 4,324,314 A | 4/1982 | Beach et al. |
| 4,405,297 A | 9/1983 | Appel |
| 4,463,045 A | 7/1984 | Ahr et al. |
| 4,573,986 A | 3/1986 | Minetola et al. |
| 4,610,678 A | 9/1986 | Weisman et al. |
| 4,629,643 A | 12/1986 | Curro |
| 4,634,440 A | 1/1987 | Widlund |
| 4,662,875 A | 5/1987 | Hirotsu et al. |
| 4,673,402 A | 6/1987 | Weisman et al. |
| 4,780,352 A | 10/1988 | Palumbo |
| 4,785,996 A | 11/1988 | Ziecker et al. |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Molloy |
| 4,854,984 A | 8/1989 | Ball |
| 4,888,231 A | 12/1989 | Angstadt |
| 4,892,536 A | 1/1990 | DesMarais et al. |
| 4,894,060 A | 1/1990 | Nestegard |
| 4,919,738 A | 4/1990 | Ball et al. |
| 4,940,464 A | 7/1990 | Van Gompel et al. |
| 4,946,527 A | 8/1990 | Battrell |
| 4,990,147 A | 2/1991 | Freeland |
| 5,006,394 A | 4/1991 | Baird |
| 5,037,416 A | 8/1991 | Allen et al. |
| 5,092,861 A | 3/1992 | Nomura et al. |
| 5,137,537 A | 8/1992 | Herron et al. |
| 5,143,679 A | 9/1992 | Weber et al. |
| 5,147,345 A | 9/1992 | Young et al. |
| 5,149,720 A | 9/1992 | Desmarais |
| 5,151,092 A | 9/1992 | Buell et al. |
| 5,156,793 A | 10/1992 | Buell et al. |
| 5,167,897 A | 12/1992 | Weber et al. |
| 5,221,274 A | 6/1993 | Buell et al. |
| 5,242,436 A | 9/1993 | Weil |
| 5,246,433 A | 9/1993 | Hasse et al. |
| 5,260,345 A | 11/1993 | DesMarais et al. |
| 5,266,392 A | 11/1993 | Land |
| 5,269,775 A | 12/1993 | Freeland et al. |
| 5,342,338 A | 8/1994 | Roe |
| 5,360,420 A | 11/1994 | Cook et al. |
| 5,382,400 A | 1/1995 | Pike |
| 5,387,207 A | 2/1995 | Dyer et al. |
| 5,397,316 A | 3/1995 | Lavon et al. |
| 5,418,045 A | 5/1995 | Pike |
| 5,422,172 A | 6/1995 | Wu |
| 5,433,715 A | 7/1995 | Tanzer et al. |
| 5,518,801 A | 5/1996 | Chappell et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,155 A | 1/1997 | Nishikawa |
| 5,599,335 A | 2/1997 | Goldman et al. |
| 5,607,414 A | 3/1997 | Richards et al. |
| 5,607,760 A | 3/1997 | Roe |
| 5,609,587 A | 3/1997 | Roe |
| 5,622,772 A | 4/1997 | Stokes |
| 5,628,097 A | 5/1997 | Benson |
| 5,635,191 A | 6/1997 | Roe et al. |
| 5,643,588 A | 7/1997 | Roe et al. |
| 5,658,639 A | 8/1997 | Curro et al. |
| 5,665,300 A | 9/1997 | Brignola |
| 5,674,216 A | 10/1997 | Buell et al. |
| 5,700,254 A | 12/1997 | McDowall et al. |
| 5,702,551 A | 12/1997 | Huber et al. |
| 5,707,468 A | 1/1998 | Arnold |
| 5,817,199 A | 10/1998 | Brennecke et al. |
| 5,827,909 A | 10/1998 | Desmarais |
| 5,865,823 A | 2/1999 | Curro |
| 5,897,545 A | 4/1999 | Kline et al. |
| 5,916,661 A | 6/1999 | Benson et al. |
| 5,957,908 A | 9/1999 | Kline et al. |
| 5,968,025 A | 10/1999 | Roe et al. |
| 5,972,806 A | 10/1999 | Weinberger |
| 5,993,432 A | 11/1999 | Lodge et al. |
| 6,004,306 A | 12/1999 | Robles et al. |
| 6,036,796 A | 3/2000 | Halbert et al. |
| 6,096,668 A | 8/2000 | Abuto |
| 6,107,537 A | 8/2000 | Elder et al. |
| 6,118,041 A | 9/2000 | Roe et al. |
| 6,120,487 A | 9/2000 | Ashton |
| 6,120,489 A | 9/2000 | Johnson et al. |
| 6,123,792 A | 9/2000 | Samida |
| 6,140,551 A | 10/2000 | Niemeyer |
| 6,153,209 A | 11/2000 | Vega et al. |
| 6,169,151 B1 | 1/2001 | Waymouth |
| 6,255,236 B1 | 7/2001 | Cree |
| 6,369,121 B1 | 4/2002 | Catalfamo |
| 6,410,129 B2 | 6/2002 | Zhang et al. |
| 6,426,444 B2 | 7/2002 | Roe et al. |
| 6,432,098 B1 | 8/2002 | Kline et al. |
| 6,454,989 B1 | 9/2002 | Neely |
| 6,458,447 B1 | 10/2002 | Cabell |
| 6,465,073 B1 | 10/2002 | Morman |
| 6,472,045 B1 | 10/2002 | Morman |
| 6,472,084 B1 | 10/2002 | Middlesworth et al. |
| 6,475,600 B1 | 11/2002 | Morman |
| 6,498,284 B1 | 12/2002 | Roe |
| 6,508,641 B1 | 1/2003 | Kubik |
| 6,513,221 B2 | 2/2003 | Vogt |
| 6,518,378 B2 | 2/2003 | Waymouth |
| 6,534,149 B1 | 3/2003 | Daley et al. |
| 6,540,854 B2 | 4/2003 | Couillard |
| 6,555,643 B1 | 4/2003 | Rieger |
| 6,559,262 B1 | 5/2003 | Waymouth |
| 6,572,595 B1 | 6/2003 | Klemp et al. |
| 6,572,598 B1 | 6/2003 | Ashton |
| 6,586,652 B1 | 7/2003 | Roe et al. |
| 6,610,390 B1 | 8/2003 | Kauschke |
| 6,617,016 B2 | 9/2003 | Zhang et al. |
| 6,627,564 B1 | 9/2003 | Morman |
| 6,627,787 B1 | 9/2003 | Roe et al. |
| 6,632,386 B2 | 10/2003 | Shelley |
| 6,645,330 B2 | 11/2003 | Pargass et al. |
| 6,645,569 B2 | 11/2003 | Cramer et al. |
| 6,649,001 B2 | 11/2003 | Heden |
| 6,677,258 B2 | 1/2004 | Carroll et al. |
| 6,692,477 B2 | 2/2004 | Gibbs |
| 6,713,159 B1 | 3/2004 | Blenke et al. |
| 6,758,925 B1 | 7/2004 | Stegelmann |
| 6,767,420 B2 | 7/2004 | Stegelmann |
| 6,825,393 B2 | 11/2004 | Roe et al. |

(56) References Cited

U.S. PATENT DOCUMENTS

| | | |
|---|---|---|
| 6,830,800 B2 | 12/2004 | Curro |
| 6,843,134 B2 | 1/2005 | Anderson |
| 6,861,571 B1 | 3/2005 | Roe et al. |
| 6,863,933 B2 | 3/2005 | Cramer et al. |
| 6,878,433 B2 | 4/2005 | Curro et al. |
| 6,974,514 B2 | 12/2005 | Hamulski |
| 7,056,404 B2 | 6/2006 | McFall et al. |
| 7,062,983 B2 | 6/2006 | Anderson |
| 7,108,759 B2 | 9/2006 | You |
| 7,112,621 B2 | 9/2006 | Rohrbaugh et al. |
| 7,270,861 B2 | 9/2007 | Broering |
| 7,291,239 B2 | 11/2007 | Polanco |
| 7,435,243 B2 | 10/2008 | Miyamoto |
| 7,531,233 B2 | 5/2009 | Kling |
| 7,569,039 B2 | 8/2009 | Matsuda et al. |
| 7,572,249 B2 | 8/2009 | Betts |
| 7,582,075 B2 | 9/2009 | Betts |
| 7,625,363 B2 | 12/2009 | Yoshimasa |
| 7,741,235 B2 | 6/2010 | Hashimoto |
| 7,803,244 B2 | 9/2010 | Siqueira |
| 7,806,883 B2 | 10/2010 | Fossum et al. |
| 7,819,853 B2 | 10/2010 | Desai et al. |
| 7,824,594 B2 | 11/2010 | Qureshi et al. |
| 7,870,651 B2 | 1/2011 | Middlesworth |
| 7,896,641 B2 | 3/2011 | Qureshi et al. |
| 7,917,985 B2 | 4/2011 | Dorsey |
| 7,931,632 B2 | 4/2011 | Betts |
| 7,954,213 B2 | 6/2011 | Mizutani |
| 7,998,127 B2 | 8/2011 | Betts |
| 8,062,279 B2 | 11/2011 | Miyamoto |
| 8,062,572 B2 | 11/2011 | Qureshi et al. |
| 8,092,438 B2 | 1/2012 | Betts |
| 8,118,801 B2 | 2/2012 | Macura et al. |
| 8,158,043 B2 | 4/2012 | Gibson |
| 8,172,971 B2 | 5/2012 | Yamamoto |
| 8,186,296 B2 | 5/2012 | Brown et al. |
| 8,361,913 B2 | 1/2013 | Siqueira |
| 8,450,557 B2 | 5/2013 | Nishitani |
| 8,454,571 B2 | 6/2013 | Rezai et al. |
| 8,480,642 B2 | 7/2013 | Betts |
| 8,491,557 B2 | 7/2013 | Kline |
| 8,491,742 B2 | 7/2013 | Waas |
| 8,496,775 B2 | 7/2013 | Deng |
| 8,502,013 B2 | 8/2013 | Zhao |
| 8,518,004 B2 | 8/2013 | Betts |
| 8,585,666 B2 | 11/2013 | Weisman et al. |
| 8,618,350 B2 | 12/2013 | Mansfield |
| 8,679,391 B2 | 3/2014 | Odonnell |
| 8,690,852 B2 | 4/2014 | Macura |
| 8,697,938 B2 | 4/2014 | Roe |
| 8,709,579 B2 | 4/2014 | Hoenigmann |
| 8,728,051 B2 | 5/2014 | Lu |
| 8,741,083 B2 | 6/2014 | Wennerback |
| 8,776,856 B2 | 7/2014 | Yamamoto |
| 8,795,809 B2 | 8/2014 | Mansfield |
| 8,858,523 B2 | 10/2014 | Sauer |
| 8,939,957 B2 | 1/2015 | Raycheck et al. |
| 8,940,116 B2 | 1/2015 | Gilgenbach |
| 9,102,132 B2 | 8/2015 | Wennerbck |
| 9,211,221 B2 | 12/2015 | Macura |
| 9,301,889 B2 | 4/2016 | Miyamoto |
| 9,358,161 B2 | 6/2016 | Lawson et al. |
| 9,434,143 B2 | 9/2016 | Sablone |
| 9,498,941 B2 | 11/2016 | Sablone |
| 9,533,067 B2 | 1/2017 | Schonbeck |
| 9,687,580 B2 | 6/2017 | Schonbeck |
| 9,724,248 B2 | 8/2017 | Hughes |
| 9,821,542 B2 | 11/2017 | Bruce |
| 10,524,964 B2 | 1/2020 | Sauer |
| 10,568,775 B2 | 2/2020 | Lenser |
| 10,568,776 B2 | 2/2020 | Lenser |
| 10,575,993 B2 | 3/2020 | Lenser |
| 10,588,789 B2 | 3/2020 | Surushe |
| 10,617,573 B2 | 4/2020 | Koshijima |
| 10,952,910 B2 | 3/2021 | Dalal et al. |
| 2001/0018579 A1 | 8/2001 | Klemp |
| 2001/0024940 A1 | 9/2001 | Cook et al. |
| 2002/0095129 A1 | 7/2002 | Friderich |
| 2002/0188268 A1 | 12/2002 | Kline |
| 2003/0021951 A1 | 1/2003 | Desai |
| 2003/0105446 A1 | 6/2003 | Hutson |
| 2003/0109843 A1* | 6/2003 | Gibbs .................. A61F 13/58 604/386 |
| 2003/0109844 A1 | 6/2003 | Gibbs |
| 2003/0120240 A1 | 6/2003 | Buell |
| 2003/0124310 A1 | 7/2003 | Ellis |
| 2003/0148684 A1 | 8/2003 | Cramer et al. |
| 2003/0233082 A1 | 12/2003 | Kline et al. |
| 2004/0082931 A1 | 4/2004 | Tani |
| 2004/0091693 A1 | 5/2004 | Thomas |
| 2004/0102125 A1 | 5/2004 | Morman |
| 2004/0112509 A1 | 6/2004 | Morman |
| 2004/0121690 A1 | 6/2004 | Mleziva |
| 2004/0182499 A1 | 9/2004 | Collier |
| 2004/0224132 A1 | 11/2004 | Roe |
| 2005/0008839 A1 | 1/2005 | Cramer et al. |
| 2005/0065487 A1 | 3/2005 | Graef et al. |
| 2005/0107764 A1 | 5/2005 | Matsuda et al. |
| 2005/0154362 A1 | 7/2005 | Warren et al. |
| 2005/0245162 A1 | 11/2005 | Mccormack |
| 2005/0287892 A1 | 12/2005 | Fouse |
| 2006/0062963 A1 | 3/2006 | Middlesworth |
| 2006/0135024 A1 | 6/2006 | Thomas |
| 2006/0148361 A1 | 7/2006 | Mccormack |
| 2006/0149209 A1 | 7/2006 | Malchow et al. |
| 2006/0287637 A1* | 12/2006 | Lam .................. A61F 13/49015 604/389 |
| 2007/0105472 A1 | 5/2007 | Marche |
| 2007/0123124 A1 | 5/2007 | Middlesworth |
| 2007/0142798 A1 | 6/2007 | Goodlander et al. |
| 2007/0142806 A1* | 6/2007 | Roe .................. A61F 13/49014 604/385.01 |
| 2007/0142825 A1 | 6/2007 | Prisco |
| 2007/0143972 A1* | 6/2007 | Kline .................. A44B 18/00 24/442 |
| 2007/0202767 A1 | 8/2007 | Anderson |
| 2007/0219521 A1 | 9/2007 | Hird |
| 2007/0249254 A1 | 10/2007 | Mansfield |
| 2007/0254176 A1 | 11/2007 | Patel |
| 2007/0254547 A1 | 11/2007 | Ducauchuis |
| 2007/0287983 A1 | 12/2007 | Lodge et al. |
| 2008/0003910 A1 | 1/2008 | Hughes |
| 2008/0003911 A1 | 1/2008 | Sabbagh |
| 2008/0051748 A1 | 2/2008 | Black |
| 2008/0076315 A1 | 3/2008 | Mccormack |
| 2008/0119102 A1 | 5/2008 | Hughes |
| 2008/0147031 A1 | 6/2008 | Long et al. |
| 2008/0241476 A1 | 10/2008 | Olguin |
| 2008/0305298 A1 | 12/2008 | Lakshmi |
| 2008/0312622 A1 | 12/2008 | Hundorf |
| 2009/0035527 A1 | 2/2009 | Kobayashi |
| 2009/0069772 A1 | 3/2009 | Sauer |
| 2009/0069778 A1 | 3/2009 | Sauer |
| 2009/0191779 A1 | 7/2009 | Cree |
| 2009/0240222 A1 | 9/2009 | Tomoko |
| 2009/0258210 A1 | 10/2009 | Muslet et al. |
| 2009/0275909 A1 | 11/2009 | Sakaguchi |
| 2009/0292266 A1 | 11/2009 | Bäck |
| 2009/0294044 A1 | 12/2009 | Gill et al. |
| 2009/0299318 A1* | 12/2009 | Faulks .................. A61F 13/4902 604/385.03 |
| 2009/0299322 A1* | 12/2009 | Faulks .................. A61F 13/565 604/386 |
| 2009/0325447 A1 | 12/2009 | Austin |
| 2009/0325448 A1 | 12/2009 | Welch |
| 2010/0018579 A1 | 1/2010 | Curran |
| 2010/0062231 A1 | 3/2010 | Abed |
| 2010/0076390 A1 | 3/2010 | Norrby |
| 2010/0090363 A1 | 4/2010 | Larsen |
| 2010/0104830 A1 | 4/2010 | Jaeger |
| 2010/0112313 A1 | 5/2010 | Nakakado |
| 2010/0168704 A1 | 7/2010 | Thomas |
| 2010/0217223 A1 | 8/2010 | Kline et al. |
| 2010/0262105 A1 | 10/2010 | Turner |

(56) References Cited

U.S. PATENT DOCUMENTS

| | | |
|---|---|---|
| 2010/0268183 A1 | 10/2010 | Een |
| 2010/0280481 A1* | 11/2010 | Kline ............... A61F 13/49012 604/386 |
| 2011/0004176 A1 | 1/2011 | Andersson |
| 2011/0040273 A1 | 2/2011 | Sablone |
| 2011/0046594 A1 | 2/2011 | Sablone |
| 2011/0073513 A1 | 3/2011 | Weisman et al. |
| 2011/0139657 A1 | 6/2011 | Hird |
| 2011/0139658 A1 | 6/2011 | Hird |
| 2011/0139659 A1 | 6/2011 | Hird |
| 2011/0144610 A1 | 6/2011 | Karlson |
| 2011/0152812 A1 | 6/2011 | Hird |
| 2011/0178490 A1 | 7/2011 | Lavon |
| 2011/0196332 A1 | 8/2011 | Cheng |
| 2011/0318987 A1 | 12/2011 | Ooishi |
| 2012/0045620 A1 | 2/2012 | Oba |
| 2012/0055613 A1 | 3/2012 | Back |
| 2012/0055615 A1 | 3/2012 | Back |
| 2012/0061015 A1 | 3/2012 | Lavon et al. |
| 2012/0061016 A1 | 3/2012 | Lavon et al. |
| 2012/0095429 A1 | 4/2012 | Kobayashi et al. |
| 2012/0100351 A1 | 4/2012 | Covelli |
| 2012/0116342 A1 | 5/2012 | Stjernholm |
| 2012/0141742 A1 | 6/2012 | Yamaguchi |
| 2012/0143165 A1 | 6/2012 | Macura et al. |
| 2012/0168063 A1 | 7/2012 | Beuther |
| 2012/0196091 A1 | 8/2012 | Mizutani |
| 2012/0209230 A1* | 8/2012 | Mansfield ............ A61F 13/4902 604/361 |
| 2012/0238980 A1 | 9/2012 | Lam et al. |
| 2012/0251771 A1 | 10/2012 | Wilson |
| 2012/0277713 A1 | 11/2012 | Raycheck |
| 2012/0316526 A1 | 12/2012 | Rosati et al. |
| 2012/0321839 A1 | 12/2012 | Uematsu |
| 2013/0017370 A1 | 1/2013 | Yamaguchi |
| 2013/0022784 A1 | 1/2013 | Uematsu |
| 2013/0072887 A1 | 3/2013 | LaVon et al. |
| 2013/0082418 A1 | 4/2013 | Curro et al. |
| 2013/0090623 A1 | 4/2013 | Ohashi |
| 2013/0095279 A1 | 4/2013 | Hauschildt |
| 2013/0144245 A1 | 6/2013 | Roe |
| 2013/0158497 A1 | 6/2013 | Yamaguchi |
| 2013/0164480 A1 | 6/2013 | Sakurai et al. |
| 2013/0165883 A1 | 6/2013 | Kimura |
| 2013/0178815 A1 | 7/2013 | Ohashi |
| 2013/0184665 A1 | 7/2013 | Kato |
| 2013/0211356 A1 | 8/2013 | Nishikawa et al. |
| 2013/0213547 A1 | 8/2013 | Schneider et al. |
| 2013/0218116 A1 | 8/2013 | Schneider et al. |
| 2013/0230700 A1 | 9/2013 | Schoenbeck |
| 2013/0236700 A1 | 9/2013 | Yamanaka |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0280481 A1 | 10/2013 | Mitsuno |
| 2013/0284850 A1 | 10/2013 | Lenser |
| 2013/0306226 A1 | 11/2013 | Zink et al. |
| 2014/0018222 A1 | 1/2014 | Sablone |
| 2014/0018759 A1 | 1/2014 | Jayasinghe et al. |
| 2014/0039434 A1 | 2/2014 | Xu |
| 2014/0041786 A1 | 2/2014 | Henke et al. |
| 2014/0135194 A1 | 5/2014 | Sablone |
| 2014/0148774 A1 | 5/2014 | Brown |
| 2014/0163500 A1 | 6/2014 | Roe |
| 2014/0163506 A1 | 6/2014 | Roe |
| 2014/0163511 A1 | 6/2014 | Roe et al. |
| 2014/0234575 A1 | 8/2014 | Mitsuno et al. |
| 2014/0330232 A1 | 11/2014 | Schönbeck |
| 2014/0377506 A1 | 12/2014 | Eckstein et al. |
| 2014/0377513 A1 | 12/2014 | Galie et al. |
| 2014/0378924 A1 | 12/2014 | Turner |
| 2015/0032078 A1 | 1/2015 | Collins |
| 2015/0038929 A1 | 2/2015 | Van Malderen |
| 2015/0057630 A1 | 2/2015 | Tange |
| 2015/0126955 A1 | 5/2015 | Sauer et al. |
| 2015/0147530 A1 | 5/2015 | Mitsuno |
| 2015/0147539 A1* | 5/2015 | Thomas ............... A61F 13/4902 428/196 |
| 2015/0164699 A1 | 6/2015 | Schmitz |
| 2015/0164705 A1 | 6/2015 | Thomas |
| 2015/0173961 A1 | 6/2015 | Powell et al. |
| 2015/0182387 A1 | 7/2015 | Ferrer et al. |
| 2015/0202091 A1 | 7/2015 | Sablone |
| 2015/0297419 A1 | 10/2015 | Nelson |
| 2015/0297421 A1 | 10/2015 | Nelson |
| 2015/0313774 A1 | 11/2015 | Homoelle et al. |
| 2016/0013614 A1 | 1/2016 | Moto |
| 2016/0136014 A1 | 5/2016 | Arora |
| 2016/0167334 A1 | 6/2016 | Arora |
| 2016/0206485 A1 | 7/2016 | Seitz |
| 2016/0270972 A1 | 9/2016 | Surushe et al. |
| 2016/0324697 A1 | 11/2016 | Schoenbeck |
| 2017/0027775 A1 | 2/2017 | Barnes et al. |
| 2017/0056256 A1 | 3/2017 | Smith et al. |
| 2017/0079851 A1 | 3/2017 | Greening, II |
| 2017/0079854 A1 | 3/2017 | Butler |
| 2017/0087029 A1 | 3/2017 | Nelson et al. |
| 2017/0142806 A1 | 5/2017 | Park |
| 2017/0252229 A1 | 9/2017 | Bonelli |
| 2017/0335498 A1 | 11/2017 | Hansen |
| 2018/0014979 A1 | 1/2018 | Fujita |
| 2018/0015709 A1 | 1/2018 | Takeuchi |
| 2018/0042778 A1 | 2/2018 | Lenser et al. |
| 2018/0042779 A1 | 2/2018 | Lenser et al. |
| 2018/0042780 A1 | 2/2018 | Lenser et al. |
| 2018/0042784 A1 | 2/2018 | Koshijima |
| 2018/0042785 A1 | 2/2018 | Dalal et al. |
| 2018/0042786 A1 | 2/2018 | Mueller et al. |
| 2018/0042787 A1 | 2/2018 | Leaser et al. |
| 2018/0271716 A1 | 9/2018 | Dalal et al. |
| 2018/0271717 A1 | 9/2018 | Dria et al. |
| 2018/0281296 A1 | 10/2018 | Uchida |
| 2019/0046363 A1 | 2/2019 | Lenser et al. |
| 2019/0083323 A1 | 3/2019 | Sakai |
| 2019/0110936 A1 | 4/2019 | Becker |
| 2020/0170846 A1 | 6/2020 | Lenser |
| 2020/0179179 A1 | 6/2020 | Lenser |
| 2020/0268563 A1 | 8/2020 | Lenser |
| 2021/0000656 A1 | 1/2021 | Greening, II |
| 2021/0077306 A1 | 3/2021 | Dalal et al. |
| 2021/0154059 A1 | 5/2021 | Dalal et al. |

FOREIGN PATENT DOCUMENTS

| | | |
|---|---|---|
| EP | 1263580 B1 | 9/2010 |
| EP | 1990188 B1 | 10/2012 |
| EP | 2891480 A1 | 7/2015 |
| EP | 2841364 B1 | 8/2016 |
| EP | 3246443 A1 | 11/2017 |
| EP | 2647360 B1 | 6/2018 |
| EP | 3251642 B1 | 8/2020 |
| JP | 2004223238 A | 8/2004 |
| JP | 2007521036 A | 8/2007 |
| JP | 2011139843 A | 7/2011 |
| JP | 4934835 B2 | 3/2012 |
| JP | 5036641 B2 | 7/2012 |
| JP | 2012125483 A | 7/2012 |
| JP | 2012524645 A | 10/2012 |
| JP | 6240733 B1 | 11/2017 |
| JP | 2017065142 A | 11/2018 |
| JP | 2021024454 A | 2/2021 |
| WO | 9510996 A1 | 4/1995 |
| WO | 9511652 A1 | 5/1995 |
| WO | WO 95/16746 | 6/1995 |
| WO | WO9828123 A1 | 7/1998 |
| WO | 2000045763 A1 | 8/2000 |
| WO | 2000059430 A1 | 10/2000 |
| WO | 0073031 A1 | 12/2000 |
| WO | 2002067809 A2 | 9/2002 |
| WO | 2003007864 A1 | 1/2003 |
| WO | 2004017882 A2 | 3/2004 |
| WO | WO 2004/017885 | 3/2004 |

(56) References Cited

FOREIGN PATENT DOCUMENTS

| | | |
|---|---|---|
| WO | 2004060652 A1 | 7/2004 |
| WO | 2005016211 A1 | 2/2005 |
| WO | 2006124337 A1 | 11/2006 |
| WO | 2006138725 A2 | 12/2006 |
| WO | 2007036907 A3 | 4/2007 |
| WO | 2008023291 A3 | 2/2008 |
| WO | 2008156075 A1 | 12/2008 |
| WO | WO2009146307 A1 | 12/2009 |
| WO | 2010055699 A1 | 5/2010 |
| WO | 2010118214 A1 | 10/2010 |
| WO | WO2010126415 A1 | 11/2010 |
| WO | 2010129470 A3 | 1/2011 |
| WO | 2011080643 A2 | 7/2011 |
| WO | 2011125893 A1 | 10/2011 |
| WO | 2012052172 A1 | 4/2012 |
| WO | WO2012030571 A3 | 5/2012 |
| WO | 2012112501 A1 | 8/2012 |
| WO | 2012137553 A1 | 10/2012 |
| WO | 2012154318 A1 | 11/2012 |
| WO | 2013018846 A1 | 2/2013 |
| WO | 2013027390 A1 | 2/2013 |
| WO | 2013047890 A1 | 4/2013 |
| WO | 2013132403 A1 | 9/2013 |
| WO | 2013157365 A1 | 10/2013 |
| WO | WO2013163141 A1 | 10/2013 |
| WO | 2014011839 A1 | 1/2014 |
| WO | WO2015168032 A1 | 11/2015 |
| WO | 2015195467 A1 | 12/2015 |
| WO | 2015195468 A1 | 12/2015 |
| WO | 2016073713 A1 | 5/2016 |
| WO | WO 2016/069269 | 5/2016 |
| WO | 2016109514 A1 | 7/2016 |
| WO | 2018031841 A1 | 2/2018 |
| WO | 2018183315 A1 | 10/2018 |
| WO | 2016121979 A1 | 1/2019 |
| WO | 2019089689 A2 | 5/2019 |

OTHER PUBLICATIONS

PCT International Search Report dated Sep. 22, 2017, 15 pages.
PCT International Search Report and Written Opinion, dated Sep. 25, 2017, 16 pages.
PCT International Search Report, dated Sep. 28, 2017, 15 pages.
PCT International Search Report, dated Sep. 20, 2017, 15 pages.
All Office Actions, U.S. Appl. No. 15/674,559.
All Office Actions, U.S. Appl. No. 15/674,563.
All Office Actions, U.S. Appl. No. 15/674,566.
All Office Actions, U.S. Appl. No. 15/674,575.
All Office Actions, U.S. Appl. No. 15/674,596.
All Office Actions, U.S. Appl. No. 15/674,625.
All Office Actions, U.S. Appl. No. 15/937,180.
All Office Actions, U.S. Appl. No. 15/937,235.
All Office Actions, U.S. Appl. No. 16/049,977.
All Office Actions, U.S. Appl. No. 16/741,819.
All Office Actions, U.S. Appl. No. 16/748,885.
Case 14590MQ; All Office Actions, U.S. Appl. No. 15/674,561.
Case 15168-WO; International Search Report, PCT/US2019/024011, dated Jul. 4, 2019, 14 pages.
EP Application No. 17754982.1, Third Party Observation, dated Jun. 17, 2020, 9 pages.
EP Application No. 17764961.3, Third Party Observation, dated Aug. 24, 2020, 6 pages.
International Search Report and Written Opinion, Appl. No. PCT/US2018/024549, dated May 30, 2018, 13 pages.
International Search Report, PCT/US2017/046398, dated Sep. 28, 2017, 13 pages.
International Search Report, PCT/US2017/049026, dated Oct. 19, 2017, 13 pages.
Unpublished U.S. Appl. No. 17/108,241, filed Dec. 1, 2020, to Urmish Popatlal Dalal et al.
U.S. Appl. No. 16/916,655, filed Jun. 30, 2020, Nelson Edward Greening, II et al.
Extended European Search Report and Search Opinion; Appl. No. 20183749.9; dated Nov. 9, 2020; 8 pages.
International Search Report and Written Opinion; Appl. No. PCT/US2020/070219; dated Oct. 1, 2020; 14 pages.
All Office Actions, U.S. Appl. No. 17/168,232.
All Office Actions, U.S. Appl. No. 17/327,823.
U.S. Appl. No. 17/327,823, filed May 24, 2021, to Dalal Urmish Popatlal et. al.
All Office Actions, U.S. Appl. No. 17/108,241, filed Dec. 1, 2020.

\* cited by examiner

ABSORBENT ARTICLE WITH AN EAR PORTION

FIELD OF THE INVENTION

The present invention relates to absorbent articles having ear portions, in particular stretchable ears.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Manufacturers often use extensible areas, such as stretch side panels (i.e., ears), within the article to help achieve a snug fit. When worn, the stretch ears extend the article about the hip and waist of the wearer to anchor the product in use while still allowing the wearer to move comfortably. A fastening system is typically joined to the ear to further secure the product about the wearer. Stretch ears are typically laminates of coverstock materials (such as nonwovens) and elastomeric materials. Laminates can be produced by multiple methods to achieve the desired stretch properties. For example, nonwovens and elastomeric materials can be joined by adhesive then activated. During lamination, the nonwoven and elastic layers may be joined at approximately zero relative strain (i.e., neither layer is strained to a greater extent than the other layer). Zero strain laminates are activated by a mechanical straining process, which creates separations or deformations in the nonwovens and renders the laminate elastically extensible. Although activated ears can provide high stretch, activation processes typically require extensible nonwovens, activation friendly adhesives, and high basis weight or very strong elastic materials to ensure highly stretchable ears.

Another method of forming stretch ears is extrusion lamination, wherein an elastomeric material is extruded and bonded with a nonwoven or other coverstock material immediately upon extrusion and without the use of adhesives. To provide stretch, either the elastomeric material may be stretched before bonding with nonwoven or the nonwoven is altered in a way to provide extensibility. The stretch laminates made using such process can be expensive as they require use of elastomeric material across the entire width of the laminates.

It has been proposed to create stretch laminates using ultrasonic bonding. In such instance, an elastomeric material may be stretched, then combined with nonwoven via ultrasonic bonding while in the stretched condition. These laminates can produce highly stretchable ears (depending on the level of stretch imparted in the elastomeric material) while avoiding the use of glues and mechanical activation. Further, unlike extrusion lamination, the elastomeric material need not extend across the entire width of the laminate.

However, ultrasonically bonded ears lack the strength of other ears. During application, if the ears lack necessary strength, the ear itself may break, a fastener may become detached from the ear, and/or the ear may detach from the rest of the article. Such failures render the article itself unusable. Further, fastening systems in combination with stretch ears may increase the likelihood of product failure. In use, stretch ears tend to rope (or neck down) and collapse in height due to their relatively low modulus compared to the relative high modulus of the fastening system. Fastening systems tend to bend inwards because of the roping of the stretch ear. Roping leads to reduced surface area coverage and less contact area for friction lock of the stretch ear on the wearer's body, and the bending of the fastening system leads to discomfort and strain on the wearer.

Thus, there is a continued need for stretch ears having desirable stretch balanced with adequate strength. Likewise, there is a need for a combined ear/fastening system that provides proper fit and flexibility and that minimizes undesirable roping. There is also a need to reduce costs and enhance efficiency in creating stretch ear laminates.

SUMMARY OF THE INVENTION

In an embodiment, an absorbent article comprising includes a first waist region, a second waist region, and a crotch region disposed between the first and second waist regions. The article further comprises a chassis having a topsheet, a backsheet, and an absorbent core disposed between the topsheet and backsheet; and an ear. The ear comprises a laminate having a first nonwoven and second nonwoven and an elastomeric material sandwiched between said first and second nonwovens. The laminate comprises a plurality of ultrasonic bonds. The ear also includes a first inelastic region and an elastic region. The ear is joined to the chassis in the first inelastic region. A fastening system is joined to the ear in the elastic region.

In a further embodiment, an absorbent article comprising includes a first waist region, a second waist region, and a crotch region disposed between the first and second waist regions. The article further comprises a chassis having a topsheet, a backsheet, and an absorbent core disposed between the topsheet and backsheet; and an ear. The ear comprises a laminate having a first nonwoven and second nonwoven and an elastomeric material sandwiched between said first and second nonwovens. The laminate comprises a plurality of ultrasonic bonds. Each of the first and second nonwovens have a basis weight of 17 gsm or less. The ear has an average load at break of 18 N or greater.

In another embodiment, an absorbent article comprising includes a first waist region, a second waist region, and a crotch region disposed between the first and second waist regions. The article further comprises a chassis having a topsheet, a backsheet, and an absorbent core disposed between the topsheet and backsheet; and an ear. The ear comprises a laminate having a first nonwoven and second nonwoven and an elastomeric material sandwiched between said first and second nonwovens. The laminate comprises a plurality of ultrasonic bonds. The ear comprises an Air Permeability Value of at least 1 $m^3/m^2/min$ and a Length Ratio of about 3 or less.

DETAILED DESCRIPTION OF THE INVENTION

Definitions

Figure 1:
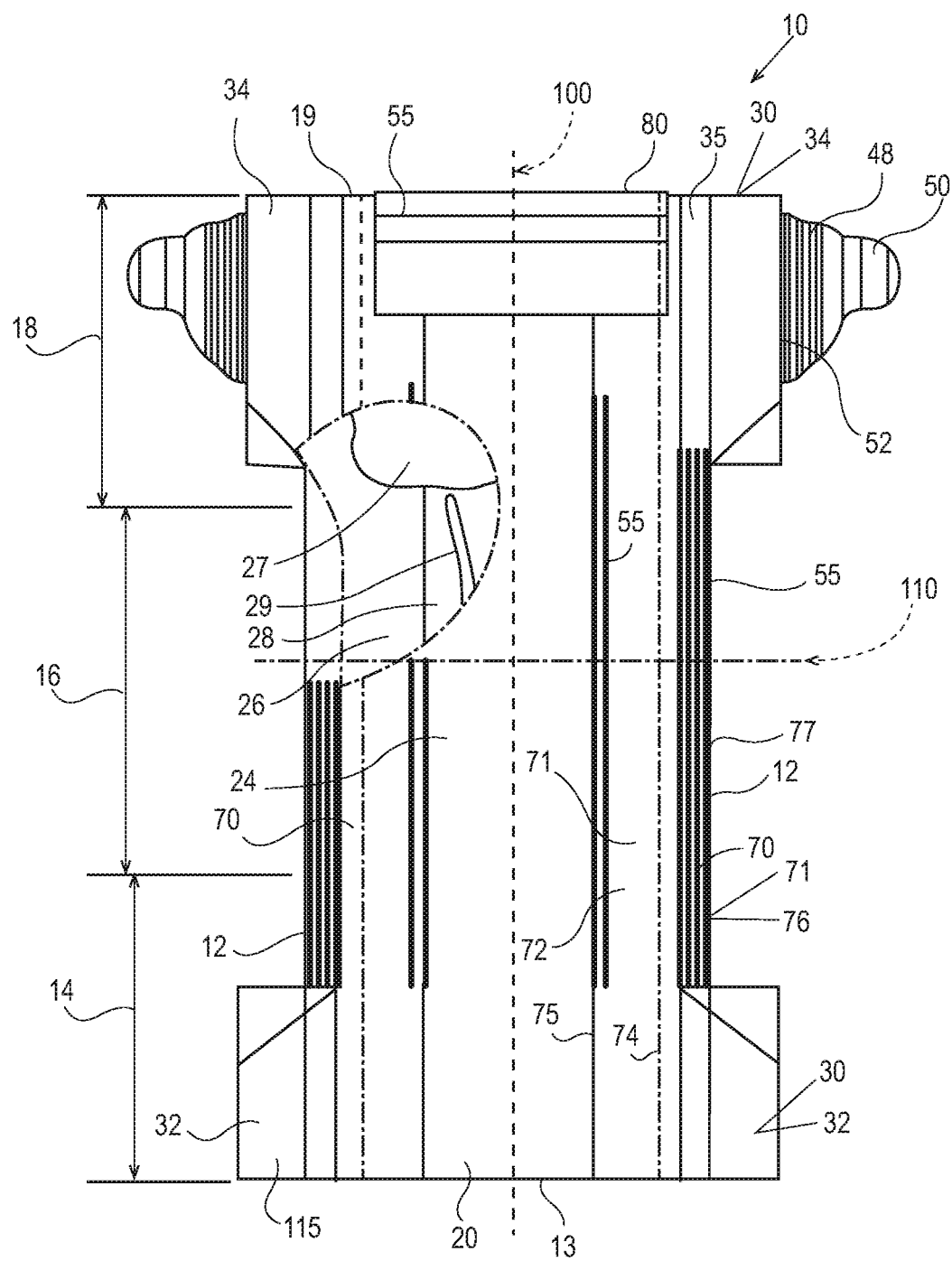
FIG. 1 is schematic plan view of an exemplary absorbent article according to one nonlimiting embodiment of the present invention. The absorbent article is shown in a flat, uncontracted state.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Activation" is the mechanical deformation of a plastically extensible material that results in permanent elongation of the extensible material, or a portion of the extensible material, in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to a plastically extensible material typically results in permanent deformation of the plastic material, while the elastic material returns substantially to its original dimension. Activation processes are disclosed for example in U.S. Pat. Pub. No. 2013/0082418, U.S. Pat. No. 5,167,897 and, U.S. Pat. No. 5,993,432.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal."

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" means a sheet-like material wherein the length and width of the material far exceed the thickness of the material (e.g., 10×, 50×, or even 1000× or more). Films are typically liquid impermeable but may be configured to be breathable.

"Laminate" means two or more materials that are bonded to one another by any suitable method known in the art (e.g., adhesive bonding, thermal bonding, ultrasonic bonding, or high pressure bonding using non-heated or heated patterned roll).

"Nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

"Relaxed" means the state of an element, material or component at rest with substantially no external force acting on the element, other than gravity.

"Elastic," "elastomeric," and "elastically extensible" mean the ability of a material to stretch by at least 100% without rupture or breakage at a given load, and upon release of the load the elastic material or component exhibits at least 80% recovery (i.e., has less than 20% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred as inelastic.

"Extensible" means the ability to stretch or elongate, without rupture or breakage, by at least 50% as per step 5(a) in the Hysteresis Test herein (replacing the specified 100% strain with 50% strain).

Absorbent Article

FIG. 1 is a plan view of an exemplary, non-limiting embodiment of an absorbent article 10 of the present invention in a flat, uncontracted state. The body-facing surface 115 of the absorbent article 10 is facing the viewer. The absorbent article 10 includes a longitudinal centerline 100 and a lateral centerline 110.

The absorbent article 10 comprises a chassis 20. The absorbent article 10 and chassis 20 are shown to have a first waist region 14, a second waist region 18 opposed to the first waist region 14, and a crotch region 16 located between the first waist region 14 and the second waist region 18. The waist regions 14 and 18 generally comprise those portions of the absorbent article 10 which, when worn, encircle the waist of the wearer. The waist regions 14 and 18 may include elastic members 55 such that they gather about the waist of the wearer to provide improved fit and containment. The crotch region 16 is the portion of the absorbent article 10 which, when the absorbent article 10 is worn, is generally positioned between the legs of the wearer.

The outer periphery of the chassis 20 is defined by longitudinal edges 12 and waist edges (first waist edge 13 in first waist region 14 and second waist edge 19 in second waist region 18). The chassis 20 may have opposing longitudinal edges 12 that are oriented generally parallel to the longitudinal centerline 100. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 110.

The chassis 20 may comprise a liquid permeable topsheet 24, a backsheet 26, and an absorbent core 28 between the topsheet 24 and the backsheet 26. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 27 is disposed between the topsheet 26 and the absorbent core 28.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Topsheet:

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core:

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. The channels may be straight, curvilinear, angled or any workable combination thereof. In one nonlimiting example, two channels are symmetrically disposed about the longitudinal axis.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Ser. Nos. 13/491,642 and 15/232,901.

Backsheet:

The backsheet 26 is generally positioned such that it may be at least a portion of the garment-facing surface of the absorbent article 10. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 10 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Ears/Fasteners:

The absorbent article 10 may include one or more ears 30, including for example front ears 32 disposed in the first waist region and/or back ears 34 disposed in the second waist region. The ears 30 may be integral with the chassis or discrete elements joined to the chassis 20 at a chassis attachment bond 35, which may join one or more layers of the ear to the chassis. The ears 30 may be extensible or elastic. The ears 30 may be formed from one or more nonwoven webs, woven webs, knitted fabrics, polymeric and elastomeric films, apertured films, sponges, foams, scrims, or combinations and/or laminates of any the foregoing.

Figure 2:
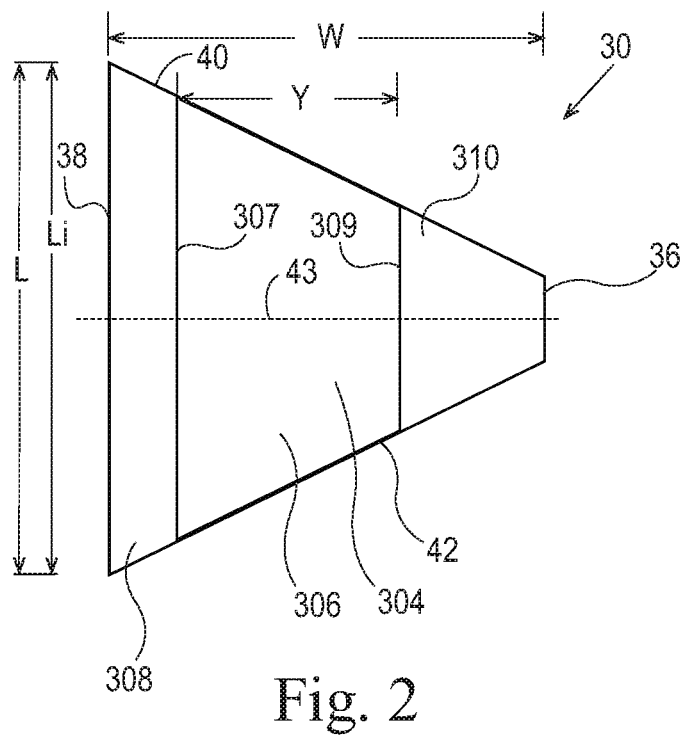
FIG. 2 is a schematic plan view of an exemplary ear according to one nonlimiting embodiment of the present invention.

As illustrated in FIG. 2, ears may include an outboard edge 36 and an inboard edge 38. The outboard edge 36 is the free distal longitudinal edge of the ear when said ear is joined to the chassis 20. The inboard edge 38 is substantially opposed to the outboard edge and is joined to or overlapped with the chassis when the ear is joined to the chassis. The inboard edge comprises a length, Li. Ears may further include a first lateral side 40 and an opposing second lateral side 42, and lateral centerline line 43 which is generally parallel to the article's lateral centerline 110 when the ear is joined to the article. An ear may additional comprise a maximum width, W, extending between the outboard edge and inboard edge and a maximum length, L, extending between the first and second lateral sides. In some embodiments, the maximum length is the length of the inboard edge, Li.

In some embodiments, the ear 30 may include elastomers, such that the ear is stretchable. In certain embodiments, the ears 30 may be formed of a stretch laminate such as a nonwoven/elastomeric material laminate or a nonwoven/elastomeric material/nonwoven laminate, which also results in the ear being stretchable. The ear 30 may be extensible in the lateral direction. In some embodiments, the ear is elastic in the lateral direction. In further embodiments, the ear 30 may extend more in the lateral direction than in the longitudinal direction. Alternatively, the ear may extend more in the longitudinal direction than in the lateral direction.

Figure 3:
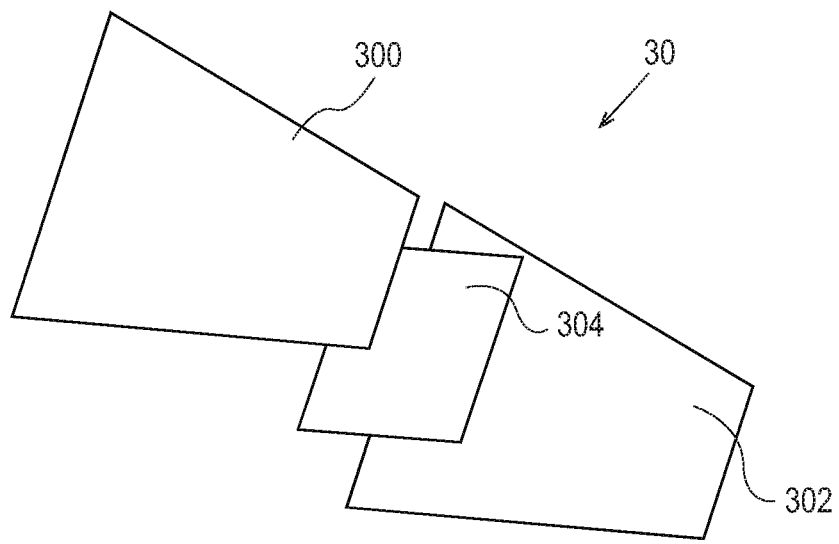
FIG. 3 is an exploded perspective view of an exemplary ear according to a nonlimiting embodiment of the present invention.

In some embodiments, the ear comprises a laminate of a first nonwoven 300 and an elastomeric layer 304. In certain embodiments illustrated in FIG. 3, an ear comprises a first nonwoven 300, a second nonwoven 302 and an elastomeric layer 304. The elastomeric layer 304 may be sandwiched between the first and second nonwovens. Additional layers may be included (e.g., additional nonwovens, inelastic materials, elastic or extensible materials, etc.).

Any suitable nonwoven may be used in an ear 30. Suitable nonwovens may comprise a basis weight of at least about 8 gsm, or less than about 22 gsm, or about 17 gsm or less, or from about 10 gsm to about 17 gsm, reciting for said range every 1 increment therein. Typically, lower basis weight nonwovens reduce an ear's overall strength. However, the inventors have discovered ears designed according to the principles herein can obtain high strength despite lower basis weight nonwovens.

Nonwoven webs can be formed by direct extrusion processes during which the fibers and webs are formed at about the same point in time, or by preformed fibers which can be laid into webs at a distinctly subsequent point in time. Example direct extrusion processes include but are not limited to: spunbonding, meltblowing, solvent spinning, electrospinning, and combinations thereof typically forming layers.

As used herein, the term "spunbonded fibers" refers to small diameter fibers, which are formed by extruding molten thermoplastic material as filaments from a plurality of fine, usually circular capillaries of a spinneret. Spunbond fibers are quenched and generally not tacky when they are deposited onto a collecting surface. Spunbond fibers are generally continuous.

As used herein, the term "meltblown fibers" means fibers formed by extruding a molten thermoplastic material through a plurality of fine, usually circular, die capillaries as molten threads or filaments into converging high velocity gas (e.g. air) streams, which attenuate the filaments of molten thermoplastic material to reduce their diameter. Thereafter, the meltblown fibers are carried by the high velocity gas stream and are deposited on a collecting surface to form a web of randomly disbursed meltblown fibers.

Example "laying" processes include wetlaying and drylaying. Example drylaying processes include but are not limited to airlaying, carding, and combinations thereof typically forming layers. Combinations of the above processes yield nonwovens commonly called hybrids or composites. Example combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers. The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof.

In some embodiments, nonwoven fabric can be unbonded nonwoven webs, electrospun nonwoven webs, flashspun nonwoven webs (e.g., TYVEK™ by DuPont), or combinations thereof. These fabrics can comprise fibers of polyolefins such as polypropylene or polyethylene, polyesters, polyamides, polyurethanes, elastomers, rayon, cellulose, copolymers thereof, or blends thereof or mixtures thereof. The nonwoven fabrics can also comprise fibers that are homogenous structures or comprise bicomponent structures such as sheath/core, side-by-side, islands-in-the-sea, and other bicomponent configurations. For a detailed description of some nonwovens, see "Nonwoven Fabric Primer and Reference Sampler" by E. A. Vaughn, Association of the Nonwoven Fabrics Indus-3d Edition (1992).

The nonwoven fabrics can include fibers or can be made from fibers that have a cross section perpendicular to the fiber longitudinal axis that is substantially non-circular. Substantially non-circular means that the ratio of the longest axis of the cross section to the shortest axis of the cross section is at least about 1.1. The ratio of the longest axis of the cross section to the shortest axis of the cross section can be about 1.1, about 1.2, about 1.5, about 2.0, about 3.0, about 6.0, about 10.0, or about 15.0. In some embodiments, this ratio can be at least about 1.2, at least about 1.5, or at least about 2.0. These ratios can be, for example, no more than about 3.0, no more than about 6.0, no more than about 10.0, or no more than about 15.0. The shape of the cross section perpendicular to the fiber longitudinal axis of the substantially non-circular fibers can be rectangular (e.g., with rounded corners) which are also referred to as "flat" fibers, trilobal, or oblong (e.g., oval) in the cross section. These substantially non-circular fibers can provide more surface area to bond to the elastomeric fiber than nonwoven fabrics with fibers that are circular in cross section. Such an increase in surface area can increase the bond strength between the fibers and a substrate.

Nonwoven softness is often associated with tactile feel. Sleek or silky feel is often preferred over rough texture. Various approaches can be used to deliver silky feel.

In one approach, nonwoven web can be made of bi-component or multi-component fibers. One of the components of the fibers, preferably outer component, is soft polymer such as polyethylene or elastic polyolefin, polyurethane. For example, in sheath/core bi-component fiber, sheath can be made of polyethylene while core can be made of polypropylene.

In another approach, nonwoven web can be made of mono-component fiber. However, fiber is made of polymer blend to impart silky soft feel. For example, polypropylene nonwoven can be coarse. However, when blended with elastomeric polypropylene (VISTAMAXX® from Exxon), it can help improve the feel of the fiber.

In another approach, nonwoven web can be made of elastomeric polymer. For example, elastomeric polyolefins are used in fibers spinning and to make nonwoven web. Such webs have very sleek feel, and elastic properties, that is often desired for consumer products.

In another approach, additives can be added to polymer before spinning fiber. During fiber spinning and subsequent process steps to make nonwoven web, the additives migrate to fiber surface to provide silky feel. Amine and Amide based additives are commonly used up to 5% to impart softness.

In another approach, sleek chemical finish can be coated on the fibers or nonwoven webs. Chemical finishes based on oil, silicone, esters, fatty acids, surfactant etc. can be employed. Softeners such as anionic, cationic or nonionic can also be used to improve drape, and touch. Various coating techniques, like roll coating, screen coating, gravure coating, slot coating, spray coating, can be used to apply finish.

In another approach, nonwoven fiber diameter can be reduced to produce fine fibers and to provide silk like feel. Meltblown fiber is one technology to reduce fiber diameter to less than 20 microns. Alternatively, nanofibers, having a diameter of less than 1 micron, made from a melt film fibrillation process with a polymer composition disclosed in U.S. Pat. No. 8,835,709 patent can be used to provide softness.

Drape is another measure of softness. Bending or pliability of material without any external force and under its own weight communicates softness. It can be influenced by variety of factors such as fiber chemistry, thickness, nonwoven bond pattern, and combinations thereof. Pliability or Drape is linked to bending stiffness, which is related to inherent elastic modulus and thickness of material. It has proven to be advantageous for the nonwoven fabric to have a minimum and a maximum bending stiffness, since for instance in the use of the nonwoven fabric in contour matching, as in medical and hygiene articles, too stiff a material would be undesirable. Polyolefin resin with lower elastic modulus and/or lower crystallinity enables lower bending stiffness. One can blend lower elastic modulus materials (elastomer) with traditional fiber making polyolefin resin to make lower modulus fibers. Optimizing bonding can also alter the bending stiffness of the web in the direction desired. Bonds with larger aspect ratio of longitudinal dimension to lateral dimension provides better drape in lateral dimension while providing right rigidity and strength for web handling. Another factor affecting drape is the thickness of the web. The thicker the web is, the lower is the flexibility or pliability. Combining right thickness with fiber chemistry or bond pattern, better drape can be achieved while delivering web performance suitable for processing.

In nonlimiting examples, a nonwoven comprises a meltblown layer. Additionally or alternatively, a nonwoven may comprise spunbond layers. In a nonlimiting example, a nonwoven comprises two or more spunbond layers. In further nonlimiting examples, one or more nonwovens may comprise a SMS configuration. Alternatively, one or more of the nonwovens in the ear may be void of meltblown layers. While meltblown layers have been found to enhance bonding in ears requiring adhesive (given the meltblown layer's inhibition of the adhesive's diffusion through the porous nonwoven structure), meltblown layers often lack strength. In some embodiments, a nonwoven consists essentially of spunbond layers. In some nonlimiting examples, both the first and the second nonwoven comprises at least 2 spunbond layers, or 3 or more spunbond layers.

Where the ear 30 comprises more than one nonwoven, the nonwovens may comprise the same basis weight or different basis weights. Likewise, the nonwovens may comprise the same layer structure or different layer structures. Further, a nonwoven in the ear may comprise the same or different features of nonwovens in the backsheet, topsheet, leg gasketing system and/or waist feature.

The elastomeric layer 304 comprises one or more elastomeric materials which provide elasticity to at least a portion of the layer 304. Nonlimiting examples of elastomeric materials include film (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, scrims, and the like. Elastomeric materials can be formed from elastomeric polymers including polymers comprising styrene derivatives, polyesters, polyurethanes, polyether amides, polyolefins, combinations thereof or any suitable known elastomers including but not limited to co-extruded VISTAMAXX®. Exemplary elastomers and/or elastomeric materials are disclosed in U.S. Pat. Nos. 8,618,350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc, Ohio), PEBAX (polyether block amide; available from Arkema Chemicals, Philadelphia, Pa.), HYTREL (polyester; available from DuPont, Wilmington, Del.), VISTAMAXX (homopolyolefins and random copolymers, and blends of random copolymers, available from EXXON Mobile, Spring, Tex.) and VERSIFY (homopolyolefins and random copolymers, and blends of random copolymers, available from Dow Chemical Company, Midland, Mich.).

In nonlimiting examples, the elastomeric layer 304 comprises a film. The film may comprise a single layer or multiple layers. The film may be elastic in the lateral direction. The elastomeric layer may comprise a width, Y, as shown for example in FIG. 2. In some embodiments, Y is less than the width, W, of the ear 30 by at least about 10 mm. The elastomeric layer may have a longitudinal dimension that is the same as the ear 30 along with the width of the elastomeric layer, or a longitudinal dimension that is less than the longitudinal length of the ear at any point along with the width of the elastomeric layer. In some embodiments, the elastomeric layer may have a basis weight of from about 5 to about 150 gsm, or from about 10 to about 100 gsm, or less than about 150 gsm, reciting for each range every 5 gsm increment therein.

As also illustrated in FIG. 2, the ear 30 may comprise an elastic region 306. The elastic region 306 is generally defined by the perimeter of the elastomeric material 304. In the elastic region, the ear is elastically extensible. In some embodiments, the area of the elastic region comprises at least about 20% of, or from about 30% to about 80% of the total area of the ear, reciting for said range every 5% increment therein. In further embodiments, Y (i.e., the maximum width of the elastomeric layer) is at least about 20% of, or from about 25% to about 85%, or from about 35% to about 80% of the total width, W, of the ear, reciting for each range every 5% increment therein. The ear further comprises one or more inelastic regions. In certain embodiments, the ear 30 comprises a first inelastic region 308, which extends laterally outward from the inboard edge 38 and is adjacent to the elastic region 306 at a first elastomeric material edge 307. The ear may further include a second inelastic region 310, which may extend laterally inward from the outboard edge 36 and may be adjacent to the elastic region 306 at a second elastomeric material edge 309. The first and second inelastic regions may be made of the same material(s) or different materials.

Figure 4:
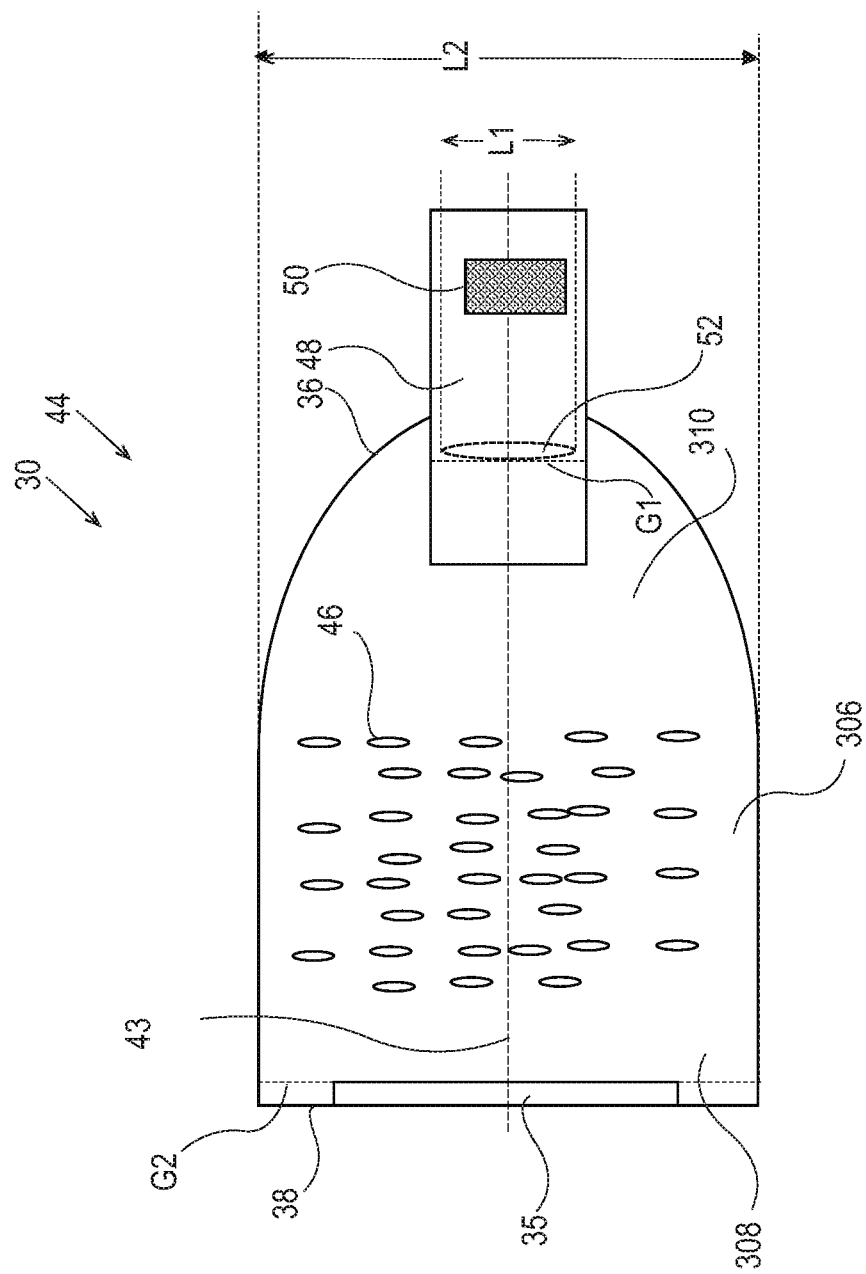
FIG. 4 is a schematic plan view of an exemplary ear according to one nonlimiting embodiment of the present invention.

Turning to FIG. 4, in certain embodiments, the ear 30 comprises a gathered laminate 44, wherein one of the layers is strained to a greater degree than a remaining layer during lamination. In this way, the less extensible layer (i.e., the nonwoven 300, 302) will form gathers when the laminate 44 is in a relaxed state. In some embodiments, the elastomeric layer is strained while the nonwoven(s) are in a relaxed state during lamination. The elastomeric layer may be stretched one or more directions. Corrugations then form in the nonwoven layer(s) when the subsequently formed laminate 44 is in a relaxed state. In nonlimiting examples, the elastomeric layer is stretched in a direction corresponding with the lateral direction of the article. In other words, when the ear is joined to the chassis subsequent to lamination, the ear laminate will be oriented such that the ear is stretchable in the lateral direction of the article. In further nonlimiting examples, the ear is also stretchable in the longitudinal direction.

The laminate layers may be joined by one or more ultrasonic bonds 46 as illustrated in FIG. 4. The ultrasonic bonds may join the nonwoven layers through the elastomeric layer. The ultrasonically bonded laminate may be formed by the process and/or equipment disclosed in commonly assigned U.S. Patent App. Nos. 62/374,010, 62/419,515.

In some embodiments, the laminate may be void of adhesive. In some nonlimiting examples, the ear comprises adhesive bond(s) only at the chassis attachment bond 35 and/or at the fastener attachment bond 52 (discussed below).

The absorbent article 10 may also include a fastening system 48. When fastened, the fastening system 48 interconnects the first waist region 14 and the rear waist region 18 resulting in a waist circumference that may encircle the wearer during wear of the absorbent article 10. The fastening system 48 may comprise a fastening elements 50 such as tape tabs, hook and loop fastening components, interlocking fasteners such as tabs & slots, buckles, buttons, snaps, and/or hermaphroditic fastening components, although any other known fastening means are generally acceptable. The absorbent article may further comprise a landing zone to which a fastening element can engage and/or a release tape that protects the fastening elements from insult prior to use. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. In some embodiments, the fastening system 48 and/or the element 50 is foldable.

Figure 5:
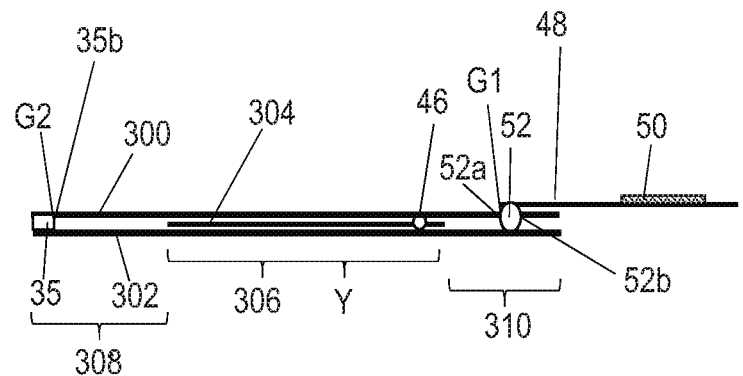
FIG. 5 is a schematic cross sectional view of the ear in FIG. 4 taken along the ear's lateral centerline.
Figure 6:
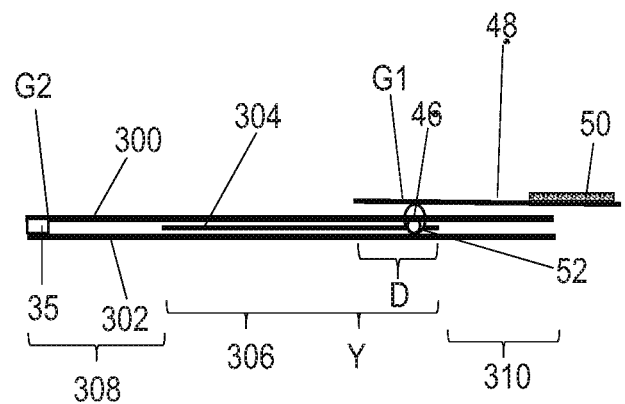
FIG. 6 is a schematic cross sectional view of an exemplary ear according to another nonlimiting embodiment of the present invention.

The fastening system 48 may be joined to any suitable portion of the article 10 by any suitable means. In some embodiments, the fastening system is joined to the ear 30 at a fastener attachment bond 52 as illustrated in FIGS. 4-6. The fastening system may be joined to the ear between layers. The fastening system may be joined to the ear on an exterior surface as shown for example in FIG. 4. In one nonlimiting example, the fastening system 48 and/or fastening elements 50 are mechanically bonded to the ear 30. In other nonlimiting examples, the fastening system and/or fastening elements may be ultrasonically bonded to the ear. The fastening attachment bond 52 comprises a maximum length, L1, measured parallel to the longitudinal centerline. The maximum length may be about 30 mm or less, or about 28 mm or less, or from about 20 mm to about 35 mm, reciting for said range every 1 mm increment therein.

Figure 7:
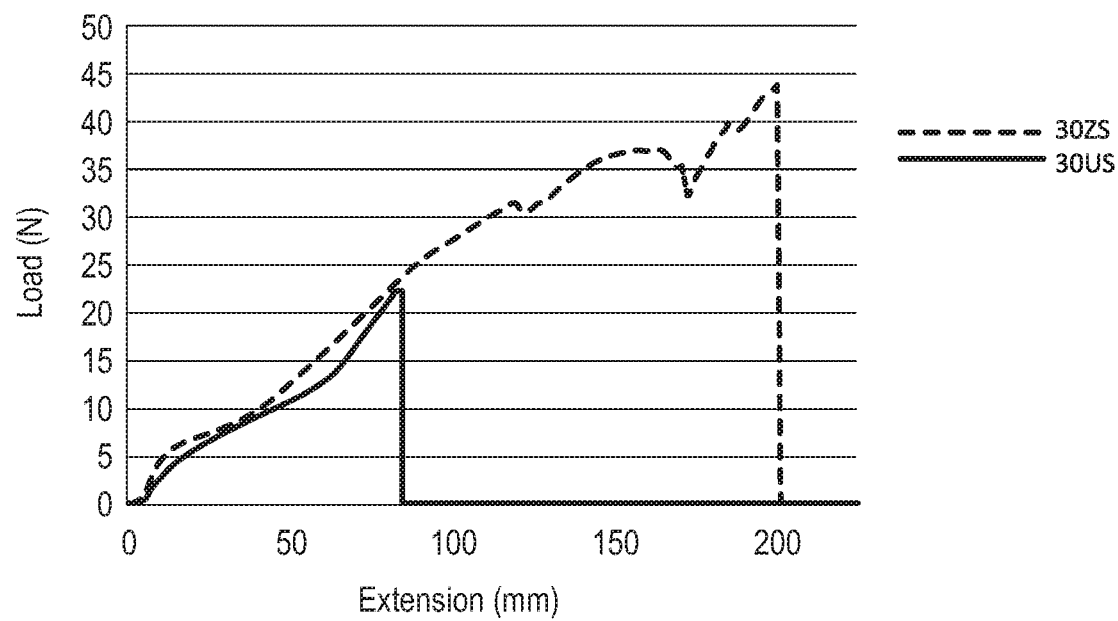
FIG. 7 is a chart showing the extension (mm) of exemplary ears versus load (N).

It has been found that ears formed from ultrasonically bonded gathered laminates exhibit less overall strength than comparable ears formed by activation. Indeed, an ear formed by zero strain activation 30ZS is compared to an ultrasonically bonded ear 30US as shown in FIG. 7. The zero strain activation processes is disclosed, for example, in U.S. Pat.

Nos. 5,167,897 and 5,156,793. The 30ZS specimen is an ear taken from a PAMPERS® CRUISERS® size 3 product, sold in the United States in July 2016. The 30US ear comprises the same materials as the 30ZS, except 30US contains no glue. During lamination of 30US, the elastomeric layer was stretched while the nonwoven layers were relaxed and the layers were joined using ultrasonic bonding. The 30US and 30ZS specimens have substantially identical dimensions. When tested using 1" top grip (to better approximate the length of fastening system attached to ear) and a 6" bottom grip using the Tensile Test Method herein, both ear laminates exhibited similar extension between 0 N and 22 N. However, the ultrasonically bonded ear tore at nearly half the load at break (N) as shown in FIG. 7. It is believed that the construction of the laminates contributes to this difference. With the activated back ear laminate, the nonwovens are broken during the activation process. Therefore, when the laminate is elongated during the Tensile Test, the elastomeric film necks down (shortens in the direction perpendicular to the elongation direction) and the broken nonwovens do not offer any resistance to such necking. Quite differently, the ultrasonically bonded ear has a substantially continuous nonwovens (in the lateral direction); and when stretched, said nonwovens resist the necking of the elastomeric layer. Further, because the film had been stretched during laminate in the ultrasonically bonded ear 30US, stretching during the Tensile Test does not result in the same level of necking as with 30ZS. The lack of necking down and/or the substantially continuous nonwovens contributes to higher stress intensification at the outboard side 36 of the ear. However, the inventors have found that designing an ultrasonically bonded ear according to the teachings herein results in increased strength, even when lower basis weight nonwovens are utilized (e.g., each nonwoven is 17 gsm or less).

Returning to FIGS. 4-6, the fastening system 48 may be joined to ear proximate to the outboard edge 36. The fastening system may be disposed in the second inelastic region 310. In further embodiments, the fastening system 48 is joined in the elastic region 306 of the ear. The inventors have found that joining the fastening system to the ear in the elastic region 306 improves the overall strength of the ear/fastening system combination during use and/or application. Without being bound by theory, it is believed that breakage in ears formed from ultrasonically bonded laminates initially occurs in an inelastic region near the outboard edge 36 as the intact nonwoven resists the stretching of the elastomeric layer; and therefore, joining the fastening system within the elastic region 306 reduces the stress on the inelastic portion of the ear. In some embodiments, the fastening system 48 is joined in the elastic region such that it overlaps with the elastic region for a maximum lateral overlap distance of D as depicted in FIG. 6. In certain nonlimiting examples, D may be from about 0.05% to about 5%, or about 1% to about 5% of Y (i.e., the maximum width of the elastic region), reciting for each range every 0.02% increment therein.

In further embodiments, the ear comprises a Length Ratio of about 3 or less, or about 2.95 or less, or from about 1 to about 3, or from about 1.75 to about 3, or from about 1 to about 2.5 as determined by the Tensile Test Method herein, reciting for each range every 0.05 interval therein. Forming an ear with such Length Ratios decreases the potential for roping within the ear. Further, the specified Length Ratios result in increased strength in the ear.

The ear may comprise an Average Load at Break of 15 N or greater, or 20 N or greater, or 25 N or greater, 30 N or greater, or 40 N or greater, or from about 15 N to about 45 N according to the Tensile Test Method herein, reciting for said range every 1 N increment therein. The specified Average Load at Break values may be obtained even when a first and second nonwovens comprise a basis weight of about 17 gsm or less, or about 14 gsm or less, or about 12 gsm or less, or from about 8 gsm to about 17 gsm, reciting for said range every 1 increment therein. Once joined to the ear, the fastening system 48 may comprise an Average Load at Break of 24 N or greater, or about 30 N or greater, or from about 17 N to about 40 N, according to the Tensile Test Method herein, reciting for said range every 1 N increment therein. The specified Average Load at Break values may be obtained even when the first and/or second nonwovens comprise a basis weight of about 17 gsm or less, or about 14 gsm or less, or about 12 gsm or less, or from about 8 gsm to about 17 gsm, reciting for said range every 1 gsm increment therein.

In certain embodiments, the ear may comprise an Air Permeability Value of at least about 1 $m^3/m^2/min$, or from about 2 $m^3/m^2/min$ to about 125 $m^3/m^2/min$, or from about 5 $m^3/m^2/min$ to about 35 $m^3/m^2/min$ according to the Air Permeability Test Method herein, reciting for each range every 2 $m^3/m^2/min$ increment therein.

Leg Gasketing System

Returning to FIG. 1, the absorbent article 10 may comprise a leg gasketing system 70 attached to the chassis 20, which may comprise one or more cuffs 71. The leg gasketing system may comprise a pair of barrier leg cuffs 72. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 24 and/or the backsheet 26 and a free terminal edge 75, which is intended to contact and form a seal with the wearer's skin. In some embodiments, the free terminal edge 75 comprises a folded edge. The barrier leg cuffs 72 extend at least partially between the front waist edge 13 and the rear waist edge 19 of the absorbent article on opposite sides of the longitudinal centerline 100 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 24 or the backsheet 26 or may be a separate material joined to the article's chassis. Each barrier leg cuff 72 may comprise one, two or more elastic elements 55 close to the free terminal edge 75 to provide a better seal.

In addition to the barrier leg cuffs 72, the article may comprise gasketing cuffs 76, which are joined to the chassis of the absorbent article, in particular to the topsheet 24 and/or the backsheet 26 and are placed externally relative to the barrier leg cuffs 72. The gasketing cuffs 76 may provide a better seal around the thighs of the wearer. A gasketing cuff may comprise a proximal edge and a free terminal edge 77. The free terminal edge 77 may comprise a folded edge. Each gasketing cuff may comprise one or more elastic elements 55 in the chassis of the absorbent article between the topsheet 24 and backsheet 26 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs.

Suitable leg gasketing systems which may be part of the absorbent article are disclosed in U.S. Pat. App. No. 62/134,622, 14/077,708; U.S. Pat. Nos. 8,939,957; 3,860,003; 7,435,243; 8,062,279.

Elastic Waist Feature

The absorbent article 10 may comprise at least one elastic waist feature 80 that helps to provide improved fit and containment, as shown in FIG. 1. The elastic waist feature 80 is generally intended to expand and contract to dynamically fit the wearer's waist. Elasticized waist features include waistbands, waist cuffs having pockets formed from a portion of the waist feature 80 that is unattached from the chassis 20, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 80 may be joined to the chassis 20 in the first waist region 14 and/or in the second waist region 18. The waist feature can be used in conjunction with the ear 30 to provide desirable stretch and flexibility for proper fit of the article on the wearer.

EXAMPLES OF EARS

Inventive Example 1

Figure 8:
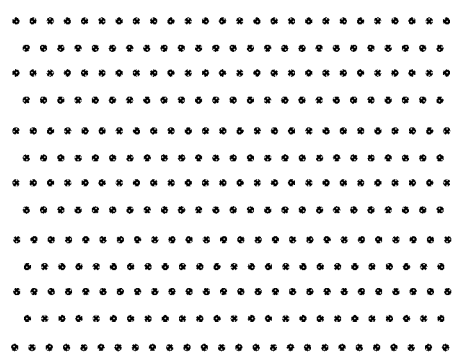
FIG. 8 is a schematic plan view of an exemplary bonding pattern according to one nonlimiting embodiment of the present invention.

Inventive Example 1 includes a first nonwoven and second nonwoven, and an elastomeric film sandwiched between the first and second nonwoven. Each of the first and second nonwoven are 17 gsm SMS available from Avgol, USA under tradename AVMN1048007001. The nonwovens have an average basis weight of 16.9±0.6 gsm as measured by the Basis Weight Test Method herein. The elastomeric film is ElastiPro™ 4407 available from Clopay, USA and has a basis weight of 53.5±1.2 gsm. The film comprises a width of 45 mm in a relaxed condition. Said film was stretched 130% strain (i.e., 45 mm stretched to about 104 mm, including a dead (unstretched) zone of 7 mm on each side) and, in its stretched state, the width grew by about 4 mm due to set. While the film was stretched as described, the first and second nonwoven were ultrasonically bonded through the film the using the bonding pattern shown in FIG. 8 and an ultrasonic bond pressure of 300N.

Inventive Example 2

Inventive Example 2 includes a first nonwoven and second nonwoven, and an elastomeric film sandwiched between the first and second nonwoven. Each of the first and second nonwoven are 14 gsm SMS available from Avgol, USA under tradename AVMN1050678001. The nonwovens have an average basis weight of 13.7±0.2 gsm as measured by the Basis Weight Test Method herein. The elastomeric film is ElastiPro™ 4407 available from Clopay, USA and has a basis weight of 53.5±1.2 gsm. The film comprises a width of 45 mm in a relaxed condition. Said film was stretched 130% strain (i.e., 45 mm stretched to about 104 mm, including a dead zone of 7 mm on each side) and, in its stretched state, the width grew by about 4 mm due to set. While the film was stretched as described, the first and second nonwoven were ultrasonically bonded through the film the using the bonding pattern shown in FIG. 8 and an ultrasonic bond pressure of 300N.

Inventive Example 3

Inventive Example 3 includes a first nonwoven and second nonwoven, and an elastomeric film sandwiched between the first and second nonwoven. Each of the first and second nonwoven are 10 gsm SMS available from Avgol, Israel under tradename AVTI1028419002. The nonwovens have an average basis weight of 10.6±0.1 gsm as measured by the Basis Weight Test Method herein. The elastomeric film is ElastiPro™ 4407 available from Clopay, USA and has a basis weight of 53.5±1.2 gsm. The film comprises a width of 45 mm in a relaxed condition. Said film was stretched 130% strain (i.e., 45 mm stretched to about 104 mm, including a dead zone of 7 mm on each side) and, in its stretched state, the width grew by about 4 mm due to set. While the film was stretched as described, the first and second nonwoven were ultrasonically bonded through the film the using the bonding pattern shown in FIG. 8 and an ultrasonic bond pressure of 300N.

Inventive Example 4

Inventive Example 4 includes a first nonwoven and second nonwoven, and an elastomeric film sandwiched between the first and second nonwoven. Each of the first and second nonwoven are 12 gsm SSS available from FQN, USA under tradename XA0048483. The nonwovens have an average basis weight of 12.9±0.3 gsm as measured by the Basis Weight Test Method herein. The elastomeric film is ElastiPro™ 4407 available from Clopay, USA and has a basis weight of 53.5±1.2 gsm. The film comprises a width of 45 mm in a relaxed condition. Said film was stretched 130% strain (i.e., 45 mm stretched to about 104 mm, including a dead zone of 7 mm on each side) and, in its stretched state, the width grew by about 4 mm due to set. While the film was stretched as described, the first and second nonwoven were ultrasonically bonded through the film the using the bonding pattern shown in FIG. 8 and an ultrasonic bond pressure of 300N.

Inventive Example 5

Inventive Example 5 includes a first nonwoven and second nonwoven, and an elastomeric film sandwiched between the first and second nonwoven. Each of the first and second nonwoven are 17 gsm SMS available from Avgol, USA under tradename AVMN1048007001. The nonwovens have an average basis weight of 16.9±0.6 gsm as measured by the Basis Weight Test Method herein. The elastomeric film is ElastiPro™ 4407 available from Clopay, USA and has a basis weight of 53.5±1.2 gsm. The film comprises a width of 36 mm in a relaxed condition. Said film was stretched 130% strain (i.e., 36 mm stretched to about 83 mm, including a dead zone of 7 mm on each side) and, in its stretched state, the width grew by about 4 mm due to set. While the film was stretched as described, the first and second nonwoven were ultrasonically bonded through the film the using the bonding pattern shown in FIG. 8 and an ultrasonic bond pressure of 300N.

Figure 9:
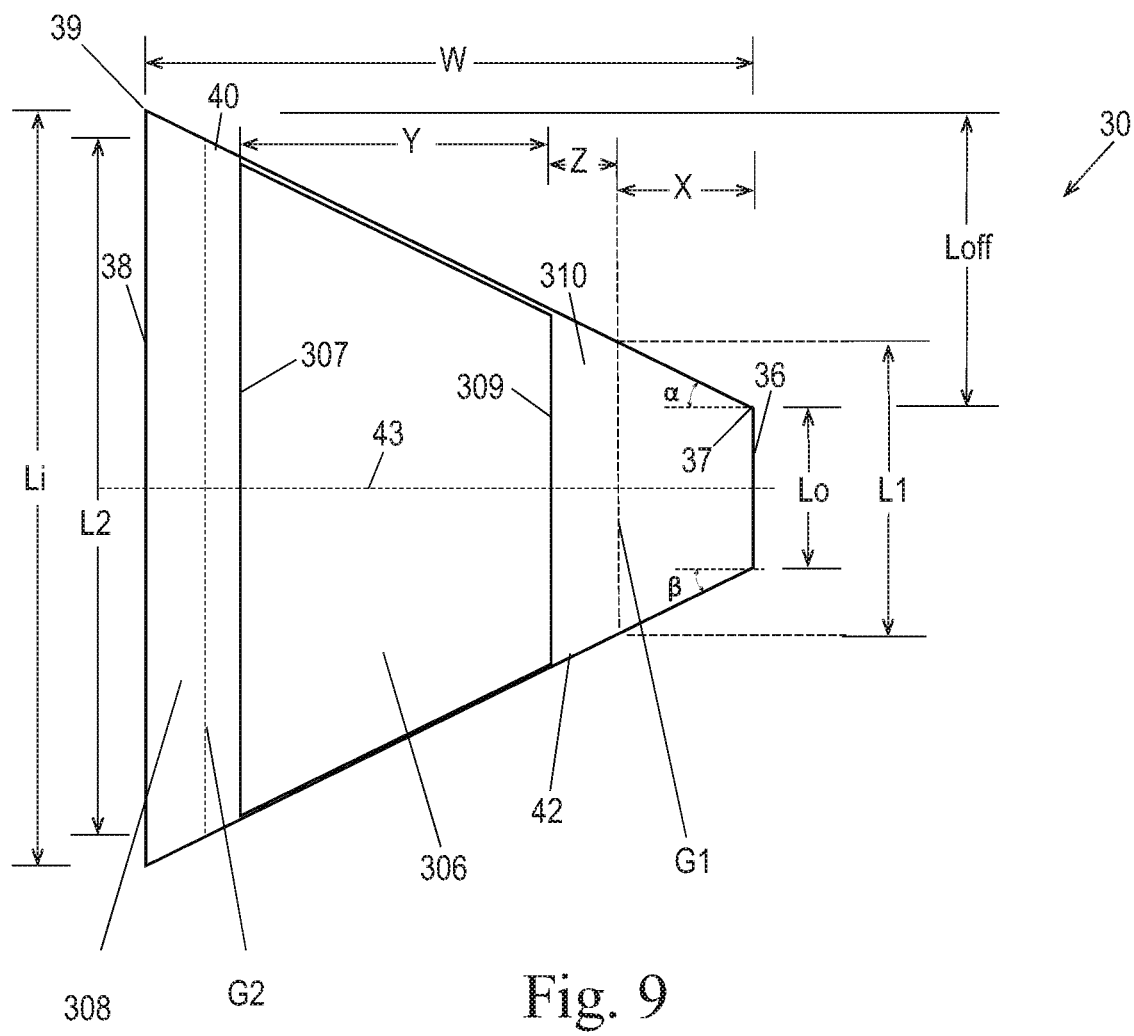
FIG. 9 is a schematic plan view of an exemplary ear shape according to one nonlimiting embodiment of the present invention.

The exemplary ears above are cut into specimens having the shapes with the dimensions detailed below in Tables 1A and 1B. The dimensions are illustrated schematically and not to scale in FIG. 9. Inventive Examples 1, 2, 3, and 4 are cut in the Base, A, B, C, and D shapes. Inventive Example 1 is also cut in shapes E and G. Inventive Example 5 is cut in the shape F. Inventive Example 5 with shape F is identical to Inventive Example 1 with shape A except the film width Y is smaller for Inventive Example 5. A die made with the respective shape is used to cut the specimen. The specimens are cut to have inelastic regions on either lateral side of the elastic region. Specimens having shapes A through F were cut with an inelastic region of at least about 10 mm as measured laterally inward from the outboard edge 36. The specimen having shape G was cut with an inelastic region of at least about 10 mm as measured laterally outward from the inboard edge 38.

In each shape, the first lateral side 40 intersects with the outboard edge 36 at a first corner 37 and the first lateral side 40 intersects with the inboard edge 38 at a second corner 39. The longitudinal distance, Loff, between said corners indicates the positioning of a fastening system (i.e., towards the top of the ear, middle of the ear etc.).

The exemplary specimens were tested to determine their Average Load at Break, Average Extensions at 5N and 10N, and/or their Average Extension at Break using the Tensile Test Method herein.

The outboard side of the specimen was mounted in the top grip at a position G1, located at the distance X in tables 1A and 1B (which corresponds to the inboard edge 52a of the fastener attachment bond 52 (see FIG. 5)). The bottom grip was mounted at a position, G2, at the gage length of 55 mm as per the Tensile Test Method.

TABLE 1A

| Legend | |
|---|---|
| Length of shape's inboard edge 38 | Li |
| Length of shape's outboard edge 36 | Lo |
| Maximum width of shape | W |
| Maximum width between outboard edge 36 and first grip position G1 | X |
| Maximum width of film | Y |
| Maximum width between first grip position G1 and outboard elastomeric material edge 309 | Z |
| *Z is negative if G1 is disposed in the elastic region | |
| Angle of slope of the first lateral side 40 | α |
| Angle of slope of the second lateral side 42 | β |
| Offset length between a first corner 37 on the outboard edge 36 and a second corner 39 on the inboard edge 38 | Loff |
| Maximum Length of the fastener attachment bond | L1 |
| *in the Inventive Examples, the length of the specimen at G1 is the same as the maximum length of the fastener attachment bond | |
| Length of the specimen at G2 | L2 |
| Length Ratio | L2:L1 |

In Table 1A, lengths are measured along a line perpendicular to the lateral centerline 43 and widths are measured along a line parallel to the lateral centerline.

Tape 1B

| | | | | | Dimensions | | | | | | |
|---|---|---|---|---|---|---|---|---|---|---|---|
| Shape | Li (mm) | Lo (mm) | W (mm) | X (mm) | Y (mm) | Z mm | α (degree) | β (degree) | Loff (mm) | L2 (mm) | L1 (mm) | L2:L1 |
| Base | 101.6 | 19.1 | 65 | 7 | 49 | 3 | 32.42 | 32.42 | 41.3 | 97.79 | 27.94 | 3.5 |
| A | 101.6 | 25.4 | 65 | 7 | 49 | 3 | 30.38 | 30.38 | 38.1 | 98.08 | 33.61 | 2.92 |
| B | 101.6 | 32 | 65 | 7 | 49 | 3 | 28.16 | 28.16 | 34.8 | 98.39 | 39.50 | 2.49 |
| C | 101.6 | 50.8 | 65 | 7 | 49 | 3 | 21.34 | 21.34 | 25.4 | 99.26 | 56.27 | 1.76 |
| D | 101.6 | 25.4 | 65 | 7 | 49 | 3 | 21.34 | 38.01 | 25.4 | 98.08 | 33.61 | 2.92 |
| E | 101.6 | 25.4 | 65 | 7 | 49 | 3 | 11.06 | 44.33 | 12.7 | 98.08 | 33.61 | 2.92 |
| F | 101.6 | 25.4 | 65 | 7 | 40 | 5 | 30.38 | 30.38 | 38.1 | 98.08 | 33.61 | 2.92 |
| G | 101.6 | 25.4 | 65 | 7 | 49 | −1 | 30.38 | 30.38 | 38.1 | 98.08 | 33.61 | 2.92 |

The Base Shape comprises dimensions commonly used in back ears in known diapers. Shapes A, D, E, and F have identical Length Ratios. However, said shapes vary in dimensions, film width and/or slope angles. Stress intensification will differ for these shapes due to different α and/or β angles and/or different film width, Y. As can be seen below, the stress intensification had little to no impact on strength.

The impact of Length Ratio was studied with Inventive Examples 1, 2, and 3 in the shapes Base, A, B, and C. Table 2 shows the Average Load at Break for each example.

TABLE 2

| | Average Load at Break (N) per given shape design | | | |
|---|---|---|---|---|
| Ear | Base (L2:L1 = 3.5) | Shape A (L2:L1 = 2.92) | Shape B (L2:L1 = 2.49) | Shape C (L2:L1 = 1.76) |
| Inventive Example 1 | 24.40 ± 1.77 | 29.74 ± 3.65 | 33.85 ± 2.43 | 45.85 ± 1.23 |
| Inventive Example 2 | 17.13 ± 1.37 | 24.99 ± 1.78 | 28.3 ± 3.96 | 36.64 ± 4.04 |
| Inventive Example 3 | 13.31 ± 0.90 | 17.02 ± 1.83 | 19.33 ± 1.46 | 27.87 ± 1.72 |

As can be seen, ear strength improves as the Length Ratio decreases even with lower basis weight nonwovens. Indeed, by decreasing the Length Ratio, an ear having 10 gsm nonwovens (Inventive Example 3) can obtain an Average Load at Break (i.e., strength) value that is comparable to a higher basis weight ear. Further, as compared to the Base, each of Shapes A, B, and C show improved strength.

It is believed that the intensification angles (α, β) have little impact on the strength of the ears. Shapes A and D have identical Length Ratios of 2.92. However, shape D has higher intensification angle. Both shapes were tested for Load at Break for Inventive Examples 1 through 4, and results are shown in the table below. Specimens failed nearly at identical Average Load at Break values as can be seen in Table 3.

TABLE 3

| | Average Load at Break (N) per given ear | | | |
|---|---|---|---|---|
| Shape Design | Inventive Example 1 | Inventive Example 2 | Inventive Example 3 | Inventive Example 4 |
| Shape A (L2:L1 = 2.92) | 29.74 ± 3.65 | 24.99 ± 1.78 | 17.02 ± 1.83 | 23.64 ± 1.02 |
| Shape D (L2:L1 = 2.92) | 30.58 ± 1.59 | 24.16 ± 2.52 | 17.51 ± 1.73 | 24.64 ± 2.51 |

Further to the above, Inventive Example 1 is cut into shape E, which has the same Length Ratio as Shape A but different intensification angles. Again, the intensification angles show little impact to strength (see Table 4). In other words, the placement of fastening systems (e.g., towards the top of the ear versus bottom of the ear) will not significantly affect the strength, provided the Length Ratio is maintained.

TABLE 4

| Ear | Average Load at Break (N) per shape design | | |
|---|---|---|---|
| | Shape A (L2:L1 = 2.92) | Shape D (L2:L1 = 2.92) | Shape E (L2:L1 = 2.92) |
| Inventive Example 1 | 29.74 ± 3.65 | 30.58 ± 1.59 | 27.51 ± 1.85 |

Inventive Example 5 is cut in the shape F. Inventive Example 5 with shape F is identical to Inventive Example 1 with shape A except that the film width, Y, is smaller for Inventive Example 5. As shown in Table 5, the film width, Y, showed little impact on
the strength. The lower film width does, however, reduce the overall extensibility of the ear.

TABLE 5

| Ear/Shape | Average Load at Break (N) | Average Extension at Load at Break (mm) |
|---|---|---|
| Inventive Example 1/Shape A | 29.74 ± 3.65 | 81.87 ± 3.29 |
| Inventive Example 5/Shape F | 30.04 ± 1.49 | 77.10 ± 1.20 |

While the examples vary in overall extensibility, all specimens show similar extension profiles. Each Inventive Example having any of shapes A-G exhibits an extension of about 20 mm or greater at 5N and about 40 mm or greater at 10 N.

Figure 10:
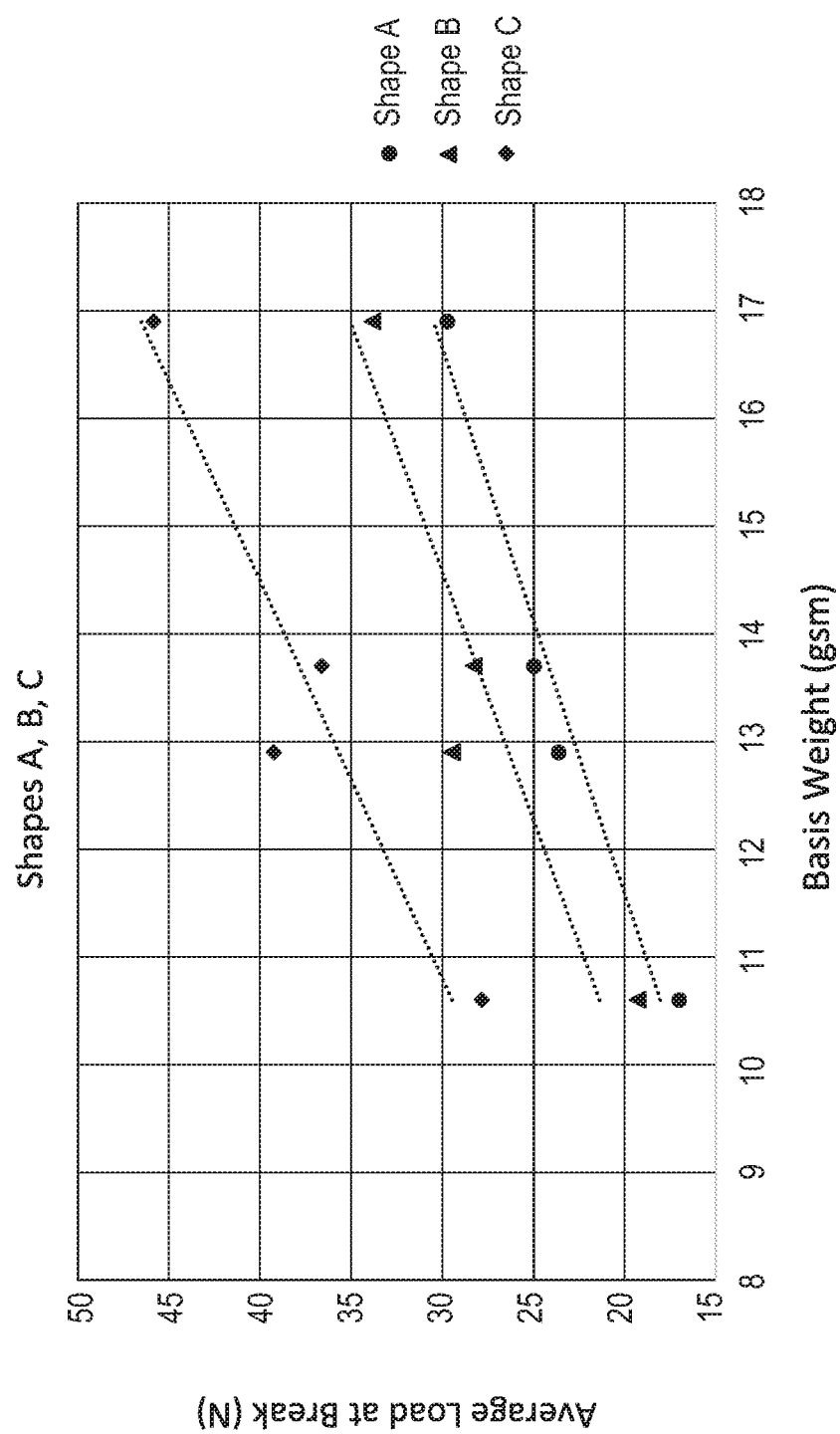
FIG. 10 is a chart showing the Average Load at Break (N) and related trendlines for ears having basis weights and shapes in accordance with nonlimiting examples of the present invention.

Further, Table 6 illustrates the difference in strength between SMS structures and SSS structures. Inventive Example 4 is made with 12 gsm SSS nonwoven on each side of the film. Eliminating layer of meltblown showed improvement in strength equivalent to a 2-4 gsm higher basis weight nonwoven with SMS construction. As the Length Ratio decreases, the strength of the SSS ear is more noticeably distinct from the SMS ear. Table 6 below and FIG. 10 compare the Average Load at Break values for Inventive Examples 1-4 in shapes A-C. As can be seen on FIG. 10, Inventive Example 4 is outside of the trendlines for each shape.

TABLE 6

| Ear | Average Load at Break (N) per given shape design | | |
|---|---|---|---|
| | Shape A (L2:L1 = 2.92) | Shape B (L2:L1 = 2.49) | Shape C (L2:L1 = 1.76) |
| Inventive Example 1 | 29.74 ± 3.65 | 33.85 ± 2.43 | 45.85 ± 1.23 |
| Inventive Example 2 | 24.99 ± 1.78 | 28.3 ± 3.96 | 36.64 ± 4.04 |
| Inventive Example 3 | 17.02 ± 1.83 | 19.33 ± 1.46 | 27.87 ± 1.72 |
| Inventive Example 4 | 23.64 ± 1.02 | 29.51 ± 1.05 | 39.26 ± 3.88 |

Table 7 compares Inventive Examples 1 and 3 in shapes A and G. Shape A and G have identical Length Ratios. However, Shape G was gripped within the elastic region during the testing. As can be seen, the Average Load at Break values were lower when the specimen is gripped inside the inelastic region (i.e., shape A). However, when the specimen is gripped 1 mm inside the elastic region (shape G), the Average Load at Break improved by at least 10%, and by at least 40% in some cases.

TABLE 7

| Ear | Average Load at Break (N) for given shape | |
|---|---|---|
| | Shape A (L2:L1 = 2.92) | Shape G (L2:L1 = 2.92) |
| Inventive Example 1 | 29.74 ± 3.65 | 35.19 ± 2.58 |
| Inventive Example 2 | 24.99 ± 1.78 | 27.78 ± 1.05 |
| Inventive Example 3 | 17.02 ± 1.83 | 24.05 ± 1.76 |

PACKAGE

The absorbent articles 10 of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 11:
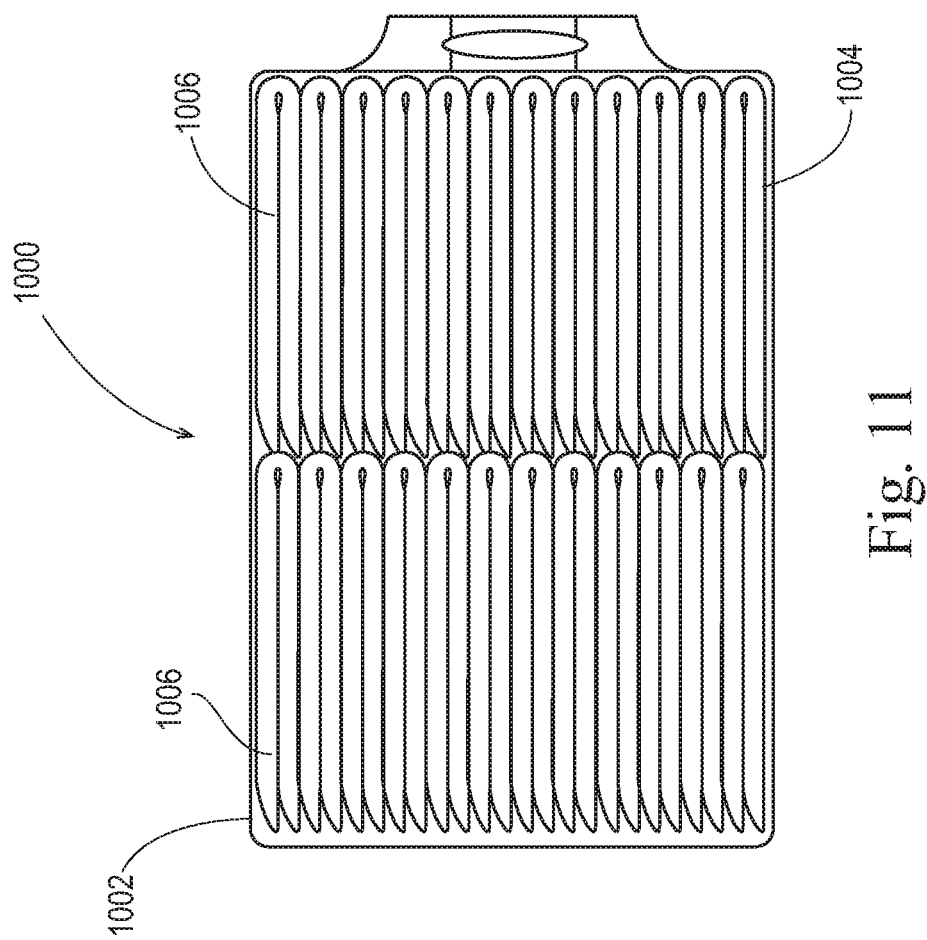
FIG. 11 is a schematic perspective view of a package in accordance with one embodiment of the present invention.

FIG. 11 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Combinations:

A. An absorbent article comprising:
   a first waist region, a second waist region, a crotch region disposed between the first and second waist regions;
   a chassis comprising a topsheet, a backsheet, and an absorbent core disposed between the topsheet and backsheet; and
   a discrete ear joined to the chassis and comprising:
   a laminate comprising a first nonwoven and second nonwoven and an elastomeric material sandwiched between said first and second nonwovens, wherein the laminate further comprises a plurality of ultrasonic bonds; and wherein first and/or second nonwoven comprises a basis weight of 17 gsm or less; and wherein the ear comprises an average load at break of 18N or greater.

B. The absorbent article of paragraph A wherein the ear comprises a first inelastic region and an elastic region, wherein the ear is joined to the chassis in the first inelastic region and wherein a fastening system is joined to the ear in the elastic region.

C. The absorbent article of paragraph B wherein the ear further comprises a second inelastic region substantially opposed to the first inelastic region, and the fastening system is disposed in both the second inelastic region and the elastic region.

D. The absorbent article any of the preceding paragraphs wherein the ear comprises a Length Ratio of about 3 or less.

E. The absorbent article of paragraph D wherein the Length Ratio is from about 1.5 to about 2.5.

F. The absorbent article of any of the preceding paragraphs wherein the fastening element comprises an average load at break of 24 N or greater.

G. The absorbent article of any of the preceding paragraphs wherein the first nonwoven and/or second nonwoven comprise a basis weight of 14 gsm or less.

H. The absorbent article of any of the preceding paragraphs wherein the first nonwoven and/or the second nonwoven consist essentially of spunbond layers.

I. The absorbent article of any of the preceding paragraphs wherein the ear is disposed in the second waist region.

J. The absorbent article of any of the preceding paragraphs wherein the ear comprises an Air Permeability Value of at least about 1.0 $m^3/m^2/min$.

K. The absorbent article of any of the preceding paragraphs wherein the ear comprises an ear area and an elastic region having an elastic region area, wherein said elastic region area is about 80% or less of the total ear area.

L. The absorbent article of any of the preceding paragraphs wherein the first nonwoven and the second nonwoven each comprise a basis weight of 14 gsm or less, and wherein the average load at break is 22 N or greater.

M. The absorbent article of any of the preceding paragraphs wherein the first nonwoven and the second nonwoven each consist essentially of spunbond layers and the average load at break is 22N or greater.

N. The absorbent article of any of the preceding paragraphs wherein the ear is extensible by 20 mm or more at 5N.

O. The absorbent article of any of the preceding paragraphs wherein the basis weight of the first and/or second nonwoven is 12 gsm or less.

P. The absorbent article of any of the preceding paragraphs wherein the average load at break is about 30 N or greater.

Q. The absorbent article of any of the preceding paragraphs wherein the basis weight of the first nonwoven is different than the basis weight of the second nonwoven.

R. The absorbent article of any of the preceding paragraphs wherein the ear is extensible by 50 mm or more at 10 N.

S. The absorbent article of any of the preceding paragraphs wherein the absorbent core comprises less than 10% by weight cellulosic fibers.

T. The absorbent article of any of the preceding paragraphs further comprising an elasticized waist feature.

U. A package comprising the absorbent article according to any of the preceding paragraphs and having an In-Bag Stack Height of less than about 110 mm.

V. The absorbent article of any of the preceding paragraphs wherein the basis weight of the first and/or second nonwoven is 10 gsm or less.

TEST METHODS

Tensile Test Method

Figure 13:
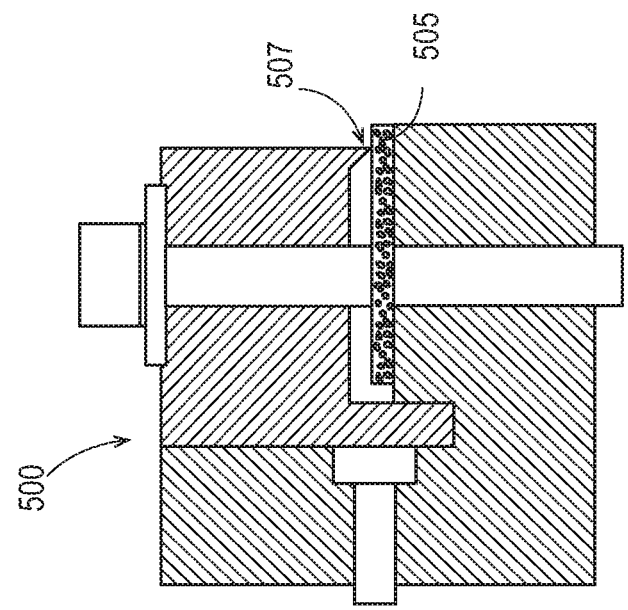
FIG. 13 is a schematic side elevation view of a grip suitable for use in the Tensile Test Method herein.
Figure 12:
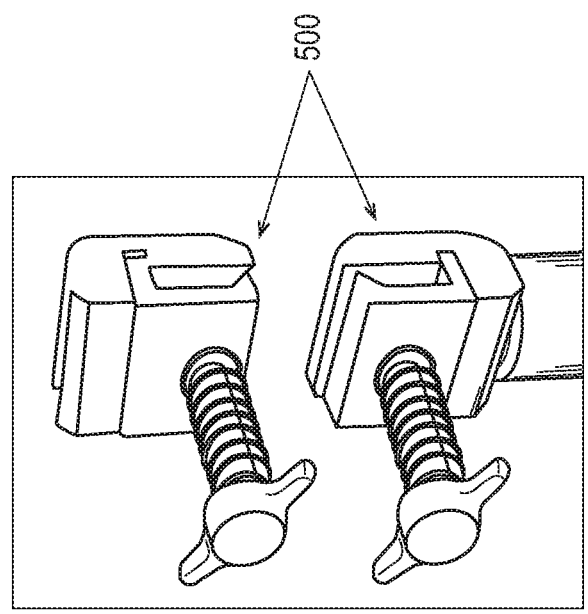
FIG. 12 is a schematic perspective view of grips suitable for use in the Tensile Test Method herein.

The Tensile Test is used to measure the strength of a specimen at a relatively high strain rate that represents product application. The method uses a suitable tensile tester such as an MTS 810, available from MTS Systems Corp., Eden Prairie Minn., or equivalent, equipped with a servo-hydraulic actuator capable of speeds exceeding 5 m/s after 28 mm of travel, and approaching 6 m/s after 40 mm of travel. The tensile tester is fitted with a 50 lb. force transducer (e.g., available from Kistler North America, Amherst, N.Y. as product code 9712 B50 (50 lb)), and a signal conditioner with a dual mode amplifier (e.g., available from Kistler North America as product code 5010). Grips shown in the FIGS. 12 and 13 should be used to secure the specimens during tensile testing. (FIG. 13 is a side view of one of the grips in FIG. 12 with a material 505 to prevent slippage.) The opposing grips 500 may have the same width or different widths as specified.

(a) Grips

The line grips 500 are selected to provide a well-defined gauge and avoid undue slippage. The specimen is positioned such that it has minimal slack between the grips. The apexes 507 of the grips 500 are ground to give good gage definition while avoiding damage or cutting of the specimen. The apexes are ground to provide a radius in the range of 0.5-1.0 mm. A portion of one or both grips 500 may be configured to include a material 505 that reduces the tendency of a specimen to slip, (e.g., a piece of urethane or neoprene rubber having a Shore A hardness of between 50 and 70) as shown in FIG. 13. Six inches wide top and bottom grips are used to clamp the specimen unless specified otherwise.

(b) Tensile Test of Specimen from Absorbent Article

Ears are generally bonded to chassis via thermal or adhesive or similar bonding. Ears should be separated from the chassis in a way that ears are not damaged and performance of the ear is not altered. If the chassis bond is too strong (i.e., ears will be damaged upon removal), then the portion of the chassis joined to the ear should be cut within the chassis material but without damaging the ear. Folded fastening systems (e.g., release tapes covering fastening elements) should be unfolded.

The specimen is clamped in the top grip at a first grip location G1 which is inboard edge 52a of the fastener attachment bond 52 (see FIG. 5). The grip line G1 is kept parallel to the longitudinal centerline of the product. If the fastener attachment bond is angled, the specimen is gripped at the center of the bond region and grip line is kept parallel to the longitudinal centerline of the product at the center. The width of the top grip should be equal to the maximum length of the fastener attachment bond 52 (L1) measured parallel to the longitudinal centerline of the article. If, at the G1 position, the length of the specimen is the same as the maximum length of the fastener attachment bond, then any grip width greater than the specimen length at G1 can be used. The specimen is mounted and hung from the top grip. The opposing edge 38 of the specimen is mounted in the bottom grip in relaxed condition. The bottom grip location G2 is adjusted so the specimen is gripped at the outboard edge 35b of the chassis bond. If the chassis bond is curvilinear, the specimen is gripped at the outboard edge of the outermost bond. The bottom grip is greater than the length of the ear at the second grip location, G2. The top and bottom grips are parallel to each other.

The specimen is tested as follows: The vertical distance (perpendicular to the grip line) from the first grip location, G1, to second grip location, G2, is measured to 0.1 mm using ruler and is used as gage length for the test. The specimen is tested at a test speed that provides 9.1 sec$^{-1}$ strain rate with the gage length selected for the specimen. Test speed in mm/second is calculated by multiplying 9.1 sec$^{-1}$ by the gage length in mm. Before testing, 5 mm of slack is put between the grips.

Each specimen is pulled to break. During testing, one of the grips is kept stationary and the opposing grip is moved. The force and actuator displacement data generated during the test are recorded using a MOOG SmarTEST ONE ST003014-205 standalone controller, with the data acquisition frequency set at 1 kHz. The resulting load data may be expressed as load at break in Newton. The Extension (mm) at 5N and at 10N are also recorded. Total of five (5) specimens are run for example. The Average Load at Break and standard deviation, the Average Extension at 5N and standard deviation, and the Average Extension at 10N and standard deviation of at least 4 specimens are recorded. If, standard deviation recorded is higher than 5%, a new set of five specimens is run.

(c) Length Ratio

Per the earlier steps, the grips are positioned at a first grip location and a second grip location. The ratio of the length of the specimen at the second grip position (L2) to the maximum length of bond (L1) is Length Ratio. The respective lengths are measured to 0.1 mm accuracy using the ruler.

Basis Weight Test Method

Each specimen is weighed to within ±0.1 milligram using a digital balance. Specimen length and width are measured using digital Vernier calipers or equivalent to within ±0.1 mm. All testing is conducted at 22±2° C. and 50±10% relative humidity. Basis weight is calculated using equation below.

$$\text{Basis Weight}\left(\frac{g}{m^2}\right) = \frac{(\text{Weight of the specimen in grams})}{(\text{Length of the specimen in meter})(\text{Width of the specimen in meter})}$$

For calculating the basis weight of a substrate, a total 8 rectilinear specimens at least 10 mm×25 mm are used.

The average basis weight and standard deviation are recorded.

Nonwoven specimens from ears are obtained as follows. The specimen should be taken from a region having no additional material (i.e., only nonwoven). Each nonwoven layer is separated from the other layers of the ear without damaging or tearing the nonwoven layer. If one continuous nonwoven covers outboard and inboard inelastic regions of the ear, said nonwoven is separated from the inelastic regions and used as the specimen. If the nonwoven layer is inseparable from other ear layers, the specimen is collected from the outboard inelastic region of the ear. If the outboard inelastic region is smaller than the prescribed specimen dimensions or has additional material (other than nonwoven layers), and if the inboard inelastic region has identical nonwovens as the outboard inelastic region, then the specimen (either nonwoven layer or the combination of nonwoven layers) is collected from the inboard inelastic region. If the nonwoven layers in the inelastic region are identical and/or inseparable, then the calculated basis weight of the specimen is divided by the number of nonwoven layers to get the individual nonwoven basis weight.

Hysteresis Test Method

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The specimens are conditioned for 24 hours prior to testing.

The specimen is cut with a dimension of 10 mm in the intended stretch direction of the ear X 25.4 mm in the direction perpendicular to the intended stretch direction of the ear. A specimen is collected from either an inelastic region or from an elastic region.

Test Protocol

1. Select the appropriate grips and load cell. The grips must have flat surfaces and must be wide enough to grasp the specimen along its full width. Also, the grips should provide adequate force and suitable surface to ensure that the specimen does not slip during testing. The load cell is selected so that the tensile response from the specimen tested is between 25% and 75% of the capacity of the load cell used.

2. Calibrate the tester according to the manufacturer's instructions.

3. Set the distance between the grips (gauge length) at 7 mm.

4. Place the specimen in the flat surfaces of the grips such that the uniform width lies along a direction perpendicular to the gauge length direction. Secure the specimen in the upper grip, let the specimen hang slack, then close the lower grip. Set the slack preload at 5 gram/force This means that the data collection starts when the slack is removed (at a constant crosshead speed of 13 mm/min) with a force of 5 gram force. Strain is calculated based on the adjusted gauge length ($l_{ini}$), which is the length of the specimen in between the grips of the tensile tester at a force of 5 gram force. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.

5(a) First cycle loading: Pull the specimen to the 100% strain at a constant cross head speed of 70 mm/min. Report the stretched specimen length between the grips as $l_{max}$.

5(b) First cycle unloading: Hold the specimen at the 100% strain for 30 seconds and then return the crosshead to its starting position (0% strain or initial sample length, $l_{ini}$) at a constant cross head speed of 70 mm/min. Hold the specimen in the unstrained state for 1 minute.

5(c) Second cycle loading: Pull the specimen to the 100% strain at a constant cross head speed of 70 mm/min.

5(d) Second cycle unload: Next, hold the specimen at the 100% strain for 30 seconds and then return the crosshead to its starting position (i.e. 0% strain) at a constant cross head speed of 70 mm/min.

A computer data system records the force exerted on the sample during the test as a function of applied strain. From the resulting data generated, the following quantities are reported.

i. Length of specimen between the grips at a slack preload of 5 gram-force ($l_{ini}$) to the nearest 0.001 mm.

ii. Length of specimen between the grips on first cycle at the 100% strain ($l_{max}$) to the nearest 0.001 mm.

iii. Length of specimen between the grips at a second cycle load force of 7 gram-force ($l_{ext}$) to the nearest 0.001 mm.

iv. % Set, which is defined as $(l_{ext}-l_{ini})/(l_{max}-l_{ini})*100\%$ to the nearest 0.01%. The testing is repeated for six separate samples and the average and standard deviation reported.

Air Permeability Test

The air permeability of an ear laminate or substrate (e.g., film, nonwoven, or article component) is determined by measuring the flow rate of standard conditioned air through a test specimen driven by a specified pressure drop. This test is particularly suited to materials having relatively high permeability to gases, such as nonwovens, apertured ear laminates and the like. ASTM D737 is used, modified as follows.

A TexTest FX 3300 instrument or equivalent is used, available from Textest AG, Switzerland, or from Advanced Testing Instruments ATI in Spartanburg S.C., USA. The procedures described in the Operating Instructions for the TEXTEST FX 3300 Air Permeability Tester manual for the Air Tightness Test and the Function and Calibration Check are followed. If a different instrument is used, similar provisions for air tightness and calibration are made according to the manufacturer's instructions.

The specimen is tested while in a relaxed state.

The test pressure drop is set to 125 Pascal and the 38.3 cm² area test head (model FX 3300-5) or equivalent is used. The result is recorded to three significant digits. The average of 5 specimens is calculated and reported as the Air Permeability Value ($m^3/m^2$/min).

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 11). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
 a first waist region, a second waist region, a crotch region disposed between the first and second waist regions;
 a chassis comprising a topsheet, a backsheet, and an absorbent core disposed between the topsheet and backsheet; and
 a discrete ear joined to the chassis and comprising:
   an outboard ear edge;
   a laminate comprising a first nonwoven and second nonwoven and an elastomeric material sandwiched between said first and second nonwovens, wherein the laminate further comprises a plurality of ultrasonic bonds; and
   a first inelastic region and an elastic region, wherein the ear is joined to the chassis in the first inelastic region at a chassis attachment bond and wherein a fastening system is joined to the ear at a fastener attachment bond only in the elastic region, wherein the fastening system comprises fastening elements disposed outboard of the outboard ear edge, and wherein the fastening system overlaps with the elastic region in an overlap by a maximum distance of 5% of a width of the elastic region such that the fastening system comprises an average load at break of 24 N or greater determined using a tensile test method, wherein the fastener attachment bond is disposed in the overlap; and
  wherein the ear comprises a Length Ratio of 1.75 to 3, wherein the Length Ratio is a maximum length of the ear at an outboard edge of the chassis bond divided by a maximum length of the fastener attachment bond.

2. The absorbent article of claim 1 wherein the ear further comprises a second inelastic region substantially opposed to the first inelastic region, and the fastening system is disposed in both the second inelastic region and the elastic region.

3. The absorbent article of claim 1 wherein the first nonwoven and/or second nonwoven comprise a basis weight of 17 gsm or less.

4. The absorbent article of claim 3 wherein the first nonwoven and/or second nonwoven comprise a basis weight of 14 gsm or less.

5. The absorbent article of claim 1 wherein the first nonwoven and/or the second nonwoven consist essentially of spunbond layers.

6. The absorbent article of claim 1 wherein the ear comprises an Air Permeability Value of at least 1.0 $m^3/m^2/min$.

7. The absorbent article of claim 1 wherein the ear comprises an ear area and the elastic region comprises an elastic region area, wherein said elastic region area is 80% or less of the total ear area.

8. The absorbent article of claim 1 wherein the fastener attachment bond is an ultrasonic bond.

9. The absorbent article of claim 1 wherein the overlap is inboard of the outboard ear edge, and wherein the fastening system is joined at the fastener attachment bond only in the elastic region such that an average load at break of the ear is at least 10% greater than an average load at break of the ear with the fastening system joined at the fastener attachment bond in the first inelastic region.

10. An absorbent article comprising:
a first waist region, a second waist region, a crotch region disposed between the first and second waist regions;
a chassis comprising a topsheet, a backsheet, and an absorbent core disposed between the topsheet and backsheet; and
an ear joined to the chassis at a chassis attachment bond and comprising:
an inboard ear edge and an outboard ear edge; and
a laminate comprising a first nonwoven and second nonwoven and an elastomeric material sandwiched between said first and second nonwovens, wherein the laminate further comprises a plurality of ultrasonic bonds;
wherein the first and second nonwoven each comprise a basis weight of 17 gsm or less; and
Wherein the ear comprises a Length Ratio of 1.75 to 3, wherein the Length Ratio is a maximum length of the fastener attachment bond, wherein the fastening system comprises fastening elements disposed outboard of the outboard ear edge, and wherein the fastening system overlaps with the elastic region in an overlap by a maximum distance of 5% of a width of the elastic region such that the ear comprises an average load at break of 18 N or greater determined using a tensile test method, wherein the fastener attachment bond is at least one of an ultrasonic bond and mechanical bond and is disposed in the overlap.

11. The absorbent article of claim 10 wherein the first nonwoven and the second nonwoven each comprise a basis weight of 14 gsm or less, and wherein the average load at break is 22 N or greater.

12. The absorbent article of claim 10 wherein the first nonwoven and the second nonwoven each consist essentially of spunbond layers and the average load at break is 22 N or greater.

13. The absorbent article of claim 10 wherein the ear is extensible by 20 mm or more at 5 N.

14. The absorbent article of claim 10 wherein the basis weight of the first and/or second nonwoven is 12 gsm or less.

15. The absorbent article of claim 10 wherein the average load at break is 30 N or greater.

16. The absorbent article of claim 10 wherein the basis weight of the first nonwoven is different than the basis weight of the second nonwoven.

17. An absorbent article comprising:
a first waist region, a second waist region, a crotch region disposed between the first and second waist regions;
a chassis comprising a topsheet, a backsheet, and an absorbent core disposed between the topsheet and backsheet; and
an ear joined to the chassis at a chassis attachment bond and comprising a laminate comprising a first nonwoven and second nonwoven and an elastomeric material sandwiched between said first and second nonwovens, wherein the laminate further comprises a plurality of ultrasonic bonds; and
wherein the ear comprises an Air Permeability Value of at least 1.0 $m^3/m^2/min$ and a Length Ratio of 1.75 to 3, wherein the Length Ratio is a maximum length of the ear at an outboard edge of the chassis bond divided by a maximum length of a fastener attachment bond, wherein a fastening system is attached to the ear only in an elastic region of the ear by the fastener attachment bond, wherein the fastening system comprises fastening elements disposed outboard of an outboard ear edge, and wherein the fastener system overlaps with the elastic region in an overlap by a maximum distance of 5% of a width of the elastic region such that the fastening system comprises an average load at break of 24 N or greater determined using a tensile test method, wherein the fastener attachment bond is disposed in the overlap.

18. The absorbent article of claim 17 wherein the ear is extensible by 20 mm or more at 5 N.

19. The absorbent article of claim 18 wherein the ear is extensible by 50 mm or more at 10 N.

* * * * *